(12) United States Patent
Toy et al.

(10) Patent No.: US 8,628,552 B2
(45) Date of Patent: Jan. 14, 2014

(54) APPARATUS AND METHOD FOR ACCESSING AN INTRAPERICARDIAL SPACE

(75) Inventors: Stephanie Toy, Santa Clarita, CA (US); Joyce Tao, Arcadia, CA (US); Vivian Wong, Van Nuys, CA (US)

(73) Assignee: Pacesetter, Inc., Sylmar, CA (US)

( * ) Notice: Subject to any disclaimer, the term of this patent is extended or adjusted under 35 U.S.C. 154(b) by 184 days.

(21) Appl. No.: 13/049,791

(22) Filed: Mar. 16, 2011

(65) Prior Publication Data

US 2012/0238968 A1 Sep. 20, 2012

(51) Int. Cl.
*A61B 17/34* (2006.01)

(52) U.S. Cl.
USPC .......................................... 606/185; 606/190

(58) Field of Classification Search
USPC ................... 606/108, 184–188, 190
See application file for complete search history.

(56) References Cited

U.S. PATENT DOCUMENTS

| | | | |
|---|---|---|---|
| 5,336,252 A | 8/1994 | Cohen | |
| 5,531,780 A * | 7/1996 | Vachon | 607/120 |
| 5,931,810 A | 8/1999 | Grabek | |
| 6,231,518 B1 | 5/2001 | Grabek et al. | |
| 6,296,630 B1 * | 10/2001 | Altman et al. | 604/508 |
| 6,423,051 B1 | 7/2002 | Kaplan et al. | |
| 6,592,552 B1 | 7/2003 | Schmidt | |
| 6,666,844 B1 | 12/2003 | Igo et al. | |
| 6,918,890 B2 | 7/2005 | Schmidt | |
| 7,063,693 B2 | 6/2006 | Guenst | |
| 7,146,225 B2 | 12/2006 | Guenst et al. | |
| 7,187,971 B2 * | 3/2007 | Sommer et al. | 607/3 |
| 7,309,328 B2 | 12/2007 | Kaplan et al. | |
| 7,729,783 B2 | 6/2010 | Michels et al. | |
| 7,736,347 B2 | 6/2010 | Kaplan et al. | |
| 7,797,059 B1 | 9/2010 | Bornzin et al. | |
| 2004/0087831 A1 * | 5/2004 | Michels et al. | 600/114 |
| 2006/0247672 A1 | 11/2006 | Vidlund et al. | |
| 2006/0259017 A1 | 11/2006 | Heil, Jr. et al. | |
| 2008/0294174 A1 | 11/2008 | Bardsley et al. | |

FOREIGN PATENT DOCUMENTS

| | | | |
|---|---|---|---|
| WO | 2006116310 A2 | 11/2006 | |
| WO | 2006116310 A3 | 5/2007 | |
| WO | 2009087592 A2 | 7/2009 | |
| WO | 2009087592 A3 | 12/2009 | |
| WO | 2010065389 A2 | 6/2010 | |
| WO | 2010065389 A3 | 9/2010 | |

* cited by examiner

*Primary Examiner* — Elizabeth Houston

(57) ABSTRACT

A medical device is disclosed herein that is configured to engage and penetrate a pericardial sac. The device includes an outer tubular body, an inner tubular body, and a helical tissue engagement member. The outer tubular body includes a proximal end, a distal end and a lumen extending between the ends. The inner tubular body includes a proximal end and a distal end. The inner tubular body is located in the lumen of the outer tubular body. The proximal end of the inner tubular body is operably coupled to the proximal end of the outer tubular body. The distal end of the inner tubular body is extendable out of the distal end of the outer tubular body. The helical tissue engagement member is displaceable from a first position to a second position, the first position being in the lumen of the outer tubular body recessed relative to the distal end of the outer tubular body, and the second position extending out of the distal end of the outer tubular body. The helical tissue engagement member is also rotatable relative to the outer tubular body.

10 Claims, 21 Drawing Sheets

APPARATUS AND METHOD FOR ACCESSING AN INTRAPERICARDIAL SPACE

FIELD OF THE INVENTION

The present invention relates to medical apparatus and methods. More specifically, the present invention relates to apparatus for, and methods of, accessing an intrapericardial space.

BACKGROUND OF THE INVENTION

To gain percutaneous access into the intrapericardial space (i.e., the space between the pericardial sac and the heart wall), doctors use a sub-xiphoid puncture technique employing a 17-gauge Touhy needle. Doctors use fluoroscopic guidance to visualize the needle placement with respect to the heart. Contrast media is also used during puncture to determine if the needle has passed through the pericardial sac and is correctly located in the intrapericardial space.

For patients with pericarditis, fluid raises the pericardial sac away form the heart wall, thereby making puncture easier to achieve. However, for the patients with a normal pericardial sac and no extra fluid between the pericardial sac and the heart wall, gaining access into the intrapericardial space is difficult. This difficultly arises because: the normal pericardial sac is a thin tough connective tissue with little stretchability; the pericardial sac is slippery on, and slides over, the heart wall; and the "virtual space" that is available for puncture provides doctors with little puncture room for pressing the needle into the pericardial sac. "Virtual space" is the potential space between the two extreme limits of the epicardial surface and the pericardial sac.

The challenges of accessing an intrapericardial space of a healthy pericardium can easily result in the heart wall being punctured. While the thicker wall of the left vertical may seal up after puncture with a 17-gauge Touhy needle, punctures of the thin walled right ventricle, right atrium and left atrium will not easily seal, thereby increasing the risk for tamponade. Even if a heart wall puncture in the left ventricle is likely to seal, it is still difficult and frustrating to attempt to access the intrapericardial space, which is a virtual space in a patient with a healthy pericardium.

There is a need in the art for an apparatus that will facilitate accessing the intrapericardial space while reducing the risk of puncturing the heart wall. There is also a need in the art for a method of accessing the intrapericardial space that reduces the risk of puncturing the heart wall.

BRIEF SUMMARY OF THE INVENTION

A medical device is disclosed herein that is configured to engage and penetrate a pericardial sac. In one embodiment, the device includes an outer tubular body, an inner tubular body, and a helical tissue engagement member. The outer tubular body includes a proximal end, a distal end and a lumen extending between the ends. The inner tubular body includes a proximal end and a distal end. The inner tubular body is located in the lumen of the outer tubular body. The proximal end of the inner tubular body is operably coupled to the proximal end of the outer tubular body. The distal end of the inner tubular body is extendable out of the distal end of the outer tubular body. The helical tissue engagement member is displaceable from a first position to a second position, the first position being in the lumen of the outer tubular body recessed relative to the distal end of the outer tubular body, and the second position extending out of the distal end of the outer tubular body. The helical tissue engagement member is also rotatable relative to the outer tubular body.

A medical device is disclosed herein that is configured to engage and penetrate a tissue barrier, such as, for example, a pericardial sac, a heart septum, or tissue barrier of a neural space. In one embodiment, the device includes a helical tissue engagement member, a first tubular body and a longitudinally extending member. The helical tissue engagement member is configured to be screwed into the tissue barrier. The first tubular body includes a distal piercing tip extendable through the helical tissue engagement member. The longitudinally extending member has a distal end and is operably coupled to the helical tissue engagement member. The longitudinally extending member and helical tissue engagement member are configured to act together to pinch the tissue barrier between a portion of the helical tissue engagement member screwed into the tissue barrier and the distal end of the longitudinally extending member.

A method of accessing a location separated by a tissue barrier is also disclosed herein. For example, the tissue barrier may be a pericardial sac, a heart septum, or a tissue barrier of a neural space. In one embodiment, the method includes: providing a device including: an outer tubular body; an inner tubular body operably coupled to the outer tubular body in a lumen of the outer tubular body and longitudinally displaceable relative to the outer tubular body; a helical engagement member operably coupled to the outer tubular body in the lumen of the outer tubular body and longitudinally displaceable relative to the outer tubular body; and a pinching element operably coupled to the outer tubular body; positioning a distal end of the outer tubular body in close proximity to the tissue barrier; screwing the helical engagement member into the tissue barrier; pinching the tissue barrier between a portion of the helical engagement member screwed into the tissue barrier and the pinching element, resulting in a pinched tissue barrier; pulling the pinched tissue barrier proximally; and causing the inner tubular body to distally project from the distal end of the outer tubular body such that a piercing distal end of the inner tubular body pierces the pinched tissue barrier.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

Figure 1:
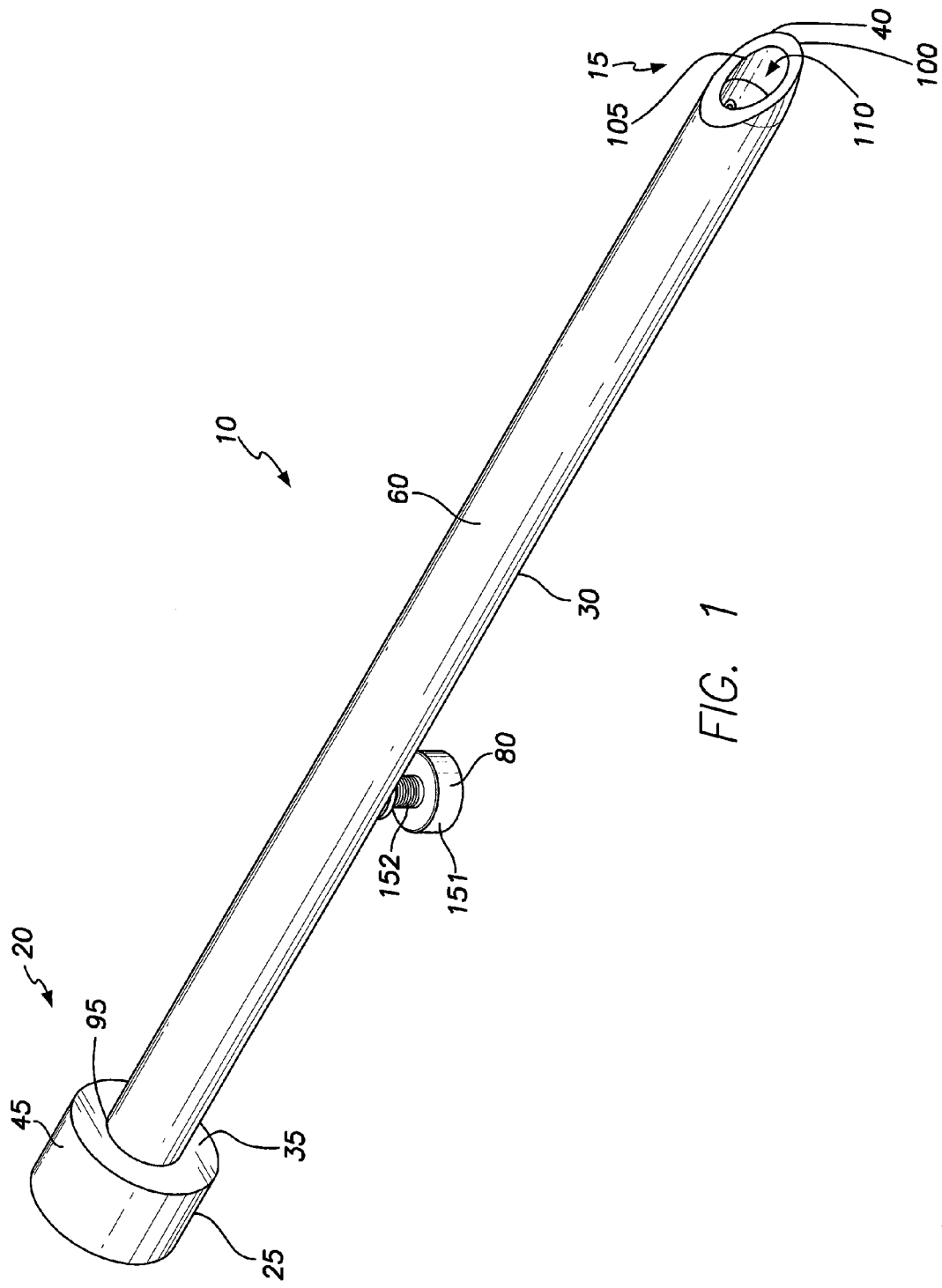
FIG. 1 is a top-side-distal isometric view of the device.

The present application describes a device and method for accessing an intrapericardial space. The device includes a tubular body assembly having an outer tubular body, at times referred to as a longitudinally extending member, and an inner tubular body coaxially positioned in the outer tubular body and longitudinally displaceable within the outer tubular body. The tubular body assembly also includes a tissue engagement spring assembly in the outer tubular body. The spring assembly includes a helical tissue engagement spring that is longitudinally displaceable, i.e., moveable along the length of the tubular body, within the outer tubular body and rotatable within the outer tubular body, about the axis of the engagement spring.

The tubular body assembly of the device is inserted into a patient via a sub-xiphoid access. The distal end of the outer tubular body is positioned against the surface of the patient's pericardial sac. The helical tissue engagement spring is longitudinally displaced in the distal direction along the length of the tubular body so as to cause at least a portion of the helical tissue engagement spring to exit a distal end of the outer tubular body. The engagement spring is rotated about its own axis to screw into the pericardial sac. Once the spring is so engaged with the pericardial sac, the spring is longitudinally displaced in the proximal direction along the length of the tubular body so as to substantially retract the spring back into the outer tubular body to pinch the pericardial sac against the distal end of the outer tubular body and the coils of the spring. The device is then used to pull the pericardial sac away from the surface of the heart wall, creating a significantly increased volume in the intrapericardial space. The inner tubular body can then be caused to distally displace within the outer tubular body to cause a sharp distal tip of the inner tubular body to protrude from the distal end of the outer tubular body and penetrate the pericardial sac in the region of the virtual space, thereby creating an access into the intrapericardial space. A guidewire, stylet, catheter, etc. can then be routed into the intrapericardial space.

Because the device can engage the pericardial sac and be used to pull the pericardial sac away from the surface of the heart wall, thereby creating a volume in the intrapericardial space that is substantial and wherein there is a substantial displacement of the pericardial sac away from the surface of the heart wall, the pericardial sac can be punctured with the device with little chance of touching the heart wall, much less puncturing or otherwise harming the heart wall. In other words, the device and method lift the pericardial sac from the underlying heart wall, thereby increasing the "virtual space" of the intrapericardial space into a volume that is adequate to allow the puncture of the sac with little risk of puncturing the underlying heart surface. Thus, the device and method are advantageous because they reduce implant time, make the physician more comfortable with accessing the intrapericardial space, reduce fluoroscopy time, increase predictability of an implant procedure, and allow the physician to puncture the pericardial sac in all four chamber zones of the heart.

Multiple embodiments of the device are disclosed herein. In a first embodiment discussed with respect to FIGS. 1-8, the helical tissue engagement spring 85 pinches the pericardial sac 208 (FIG. 10) between the coils of the spring 85 screwed into the pericardial sac and a distal end 100 of the outer tubular body 60. In a second embodiment discussed with respect to FIGS. 17-18, a separate pinching member 300 and associated assembly 302 is additionally provided, wherein the pinching member 300 of the separate pinching member assembly 302 is distally displaced to pinch the pericardial sac 208 between the distal end 308 of the pinching member and the spring 85 screwed into the pericardial sac. Finally, in a third embodiment discussed with respect to FIGS. 19-21, a separate pinching member 300 is additionally provided as part of a spring assembly 70, wherein the pinching member 300 of the spring assembly 70 is distally displaced to pinch the pericardial sac 208 between the distal end 308 of the pinching member and the spring 85 screwed into the pericardial sac.

As will be understood from the following discussion regarding the various embodiments, the device 10 may be configured to deliver a penetrating member 65 (FIG. 10) through the pericardial sac 208 via a button 56 or other member being urged distally by an operator. Alternatively, the device 10 may be configured such that the penetrating member 65 is spring loaded such that pushing a button 56 or other member simply releases a catch or other element, thereby allowing a spring 55 to rapidly bias the penetrating member distally through the pericardial sac.

Figure 2:
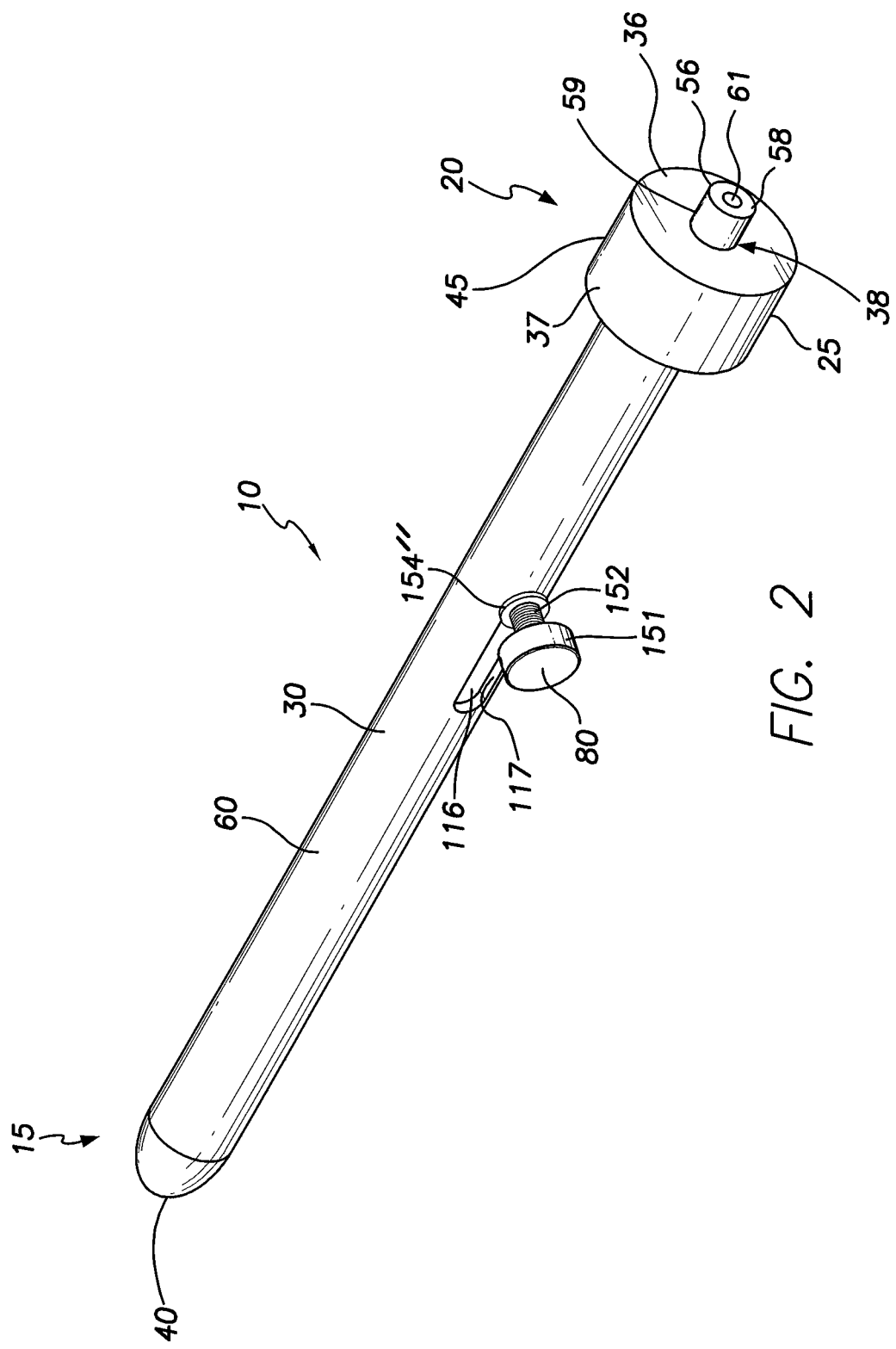
FIG. 2 is bottom-side-proximal isometric view of the device.

For a detailed discussion of the first embodiment of the device 10, reference is made to FIGS. 1 and 2, which are isometric views of the device 10 oppositely viewed. As shown in FIGS. 1 and 2, the device 10 includes a distal end 15 and a proximal end 20 opposite the distal end. A handle 25 is at the proximal end, and a tubular body assembly 30 extends distally from a distal face 35 of the handle to a distal tip 40 of the tubular body assembly 30 at the distal end 15. The handle includes a proximal face 36 and a cylindrical outer circumferential surface 37 extending between the proximal and distal faces 35, 36.

Figure 3:
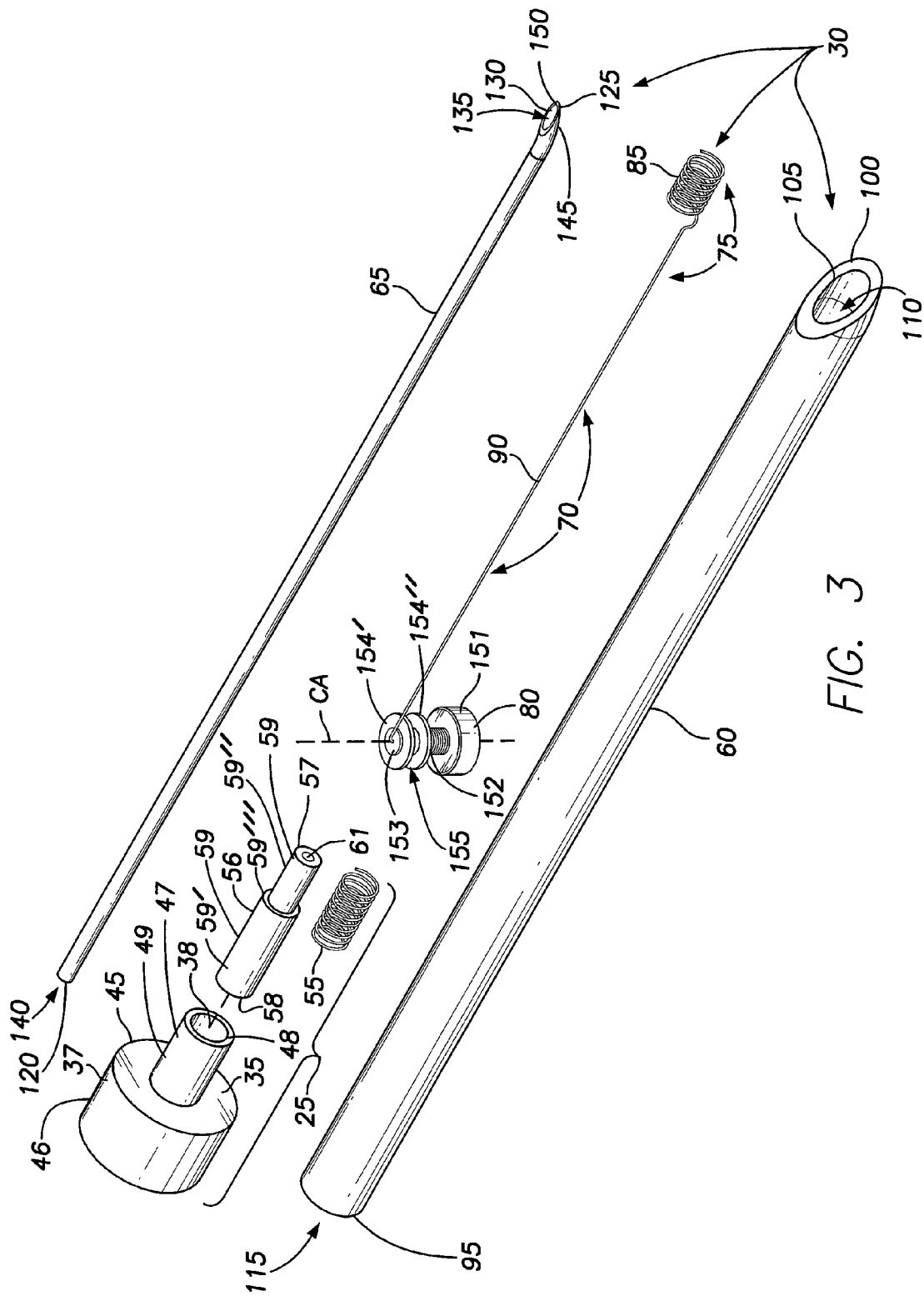
FIG. 3 is the same view as FIG. 1, except the device is in an exploded condition.

As illustrated in FIG. 3, which is the same view as FIG. 1, except the device 10 is exploded, the handle 25 of the device 10 includes an outer handle portion 45, a needle deployment button 56, and a helical spring 55 that biases the button 56 proximally relative to the outer handle portion 45. The outer handle portion 45 includes a large diameter cylindrical portion 46 and a small diameter cylindrical portion 47. The large diameter cylindrical portion includes the aforementioned distal face 35, proximal face 36, and outer circumferential surface 37, which may have a surface treatment, such as, for example, ribbing, knurling, etc. to facilitate grasping of the large diameter cylindrical portion 46.

The small diameter cylindrical portion 47 includes a distal face 48 and an outer circumferential surface 49. The small diameter cylindrical portion 47 projects distally from the distal face 35 of the large diameter cylindrical portion 46 and is generally coaxially aligned with the large diameter cylindrical portion.

The handle 25 also includes a central shaft 38 that extends proximal-distal through the handle 25 along a central axis of the handle to daylight at the proximal face 36 and the distal face 48. The shaft 38 is configured to receive the button 56 and spring 55 therein in a coaxial arrangement as discussed below.

The button 56 includes a distal end 57, a proximal end 58, and a stepped outer circumferential surface 59. The stepped outer circumferential surface includes a large diameter region 59', a small diameter region 59" and a step or shoulder 59''' separating the two regions 59', 59". The button 56 also includes a central lumen 61 that extends proximal-distal through the button 56 along a central axis of the button to daylight at the proximal face 58 and the distal face 57. The lumen 61 is configured to receive a stylet, guidewire, catheter or other tubular member therethrough as discussed below.

The tubular body assembly 30 includes an outer tubular body 60 having a longitudinal axis therethrough, an inner tubular body 65 having a longitudinal axis therethrough, and an engagement spring assembly 70. The engagement spring assembly 70 includes a tissue engagement spring 75 and a spring rotation knob 80. The tissue engagement spring 75 includes a distal region in the form of a helical section 85 having a longitudinal axis therethough and a proximal region in the form of a linear section 90 that extends proximally from a distal end of the helical section 85 and is received in the knob 80 at the longitudinally extending center axis CA of the knob 80.

The outer tubular body 60 may be in the form of a trocar or something similar and includes a blunt proximal end 95 and a beveled distal end 100, which is configured to penetrate tissue and is opposite the proximal end 95. The beveled distal end 100 may have a bevel that is between approximately 35 degrees and approximately 45 degrees from being parallel to the longitudinal center axis of the outer tubular body 60. As a result it's beveled or angled shape, the beveled distal end 100 matches the shape of the pericardium along the heart. The outer tubular body 60 includes a distal opening 105, a lumen 110, and a proximal opening 115, the lumen 110 day-lighting at the proximal and distal ends of the tubular body 60 via the openings 105, 115. The outer tubular body may be between approximately 6.0 French and approximately 5.8 French and formed of stainless steel 316 or 316L. As indicated in FIG. 2, the outer tubular body 60 also includes a longitudinally extending slot 116 defined in a circumferentially extending sidewall 117 of the outer tubular body.

The inner tubular body 65 may be in the form of a Touhy needle or something similar and includes a blunt proximal end 120 and a sharp distal end 125, which is configured to penetrate tissue and is opposite the proximal end 120. The inner tubular body 65 includes a distal opening 130, a lumen 135, and a proximal opening 140, the lumen 135 day-lighting at the proximal and distal ends of the tubular body 65 via the openings 130, 140. The inner tubular body 65 may have a slight curve 145 in its walls 150 immediately preceding the distal termination of the sharp distal end 125, the slight curve 145 resulting in the distal opening 130 opening in a direction that is generally perpendicular to a longitudinally extending center axis of the inner tubular body 65. The inner tubular body may be between approximately 3.2 French and approximately 3.5 French and formed of stainless steel 316 or 316L.

The spring rotation knob 80 includes a handle portion 151 and a shaft portion 152 extending from the handle portion in a coaxial arrangement and terminating in a free end 153. Near the free end 153 the shaft portion 152 includes first and second flanges 154', 154" spaced apart to form a gap or slot 155 between the flanges 154, the flanges extending radially outward from the shaft portion 152 in a direction generally perpendicular to the central axis CA of the shaft portion 152.

Figure 4:
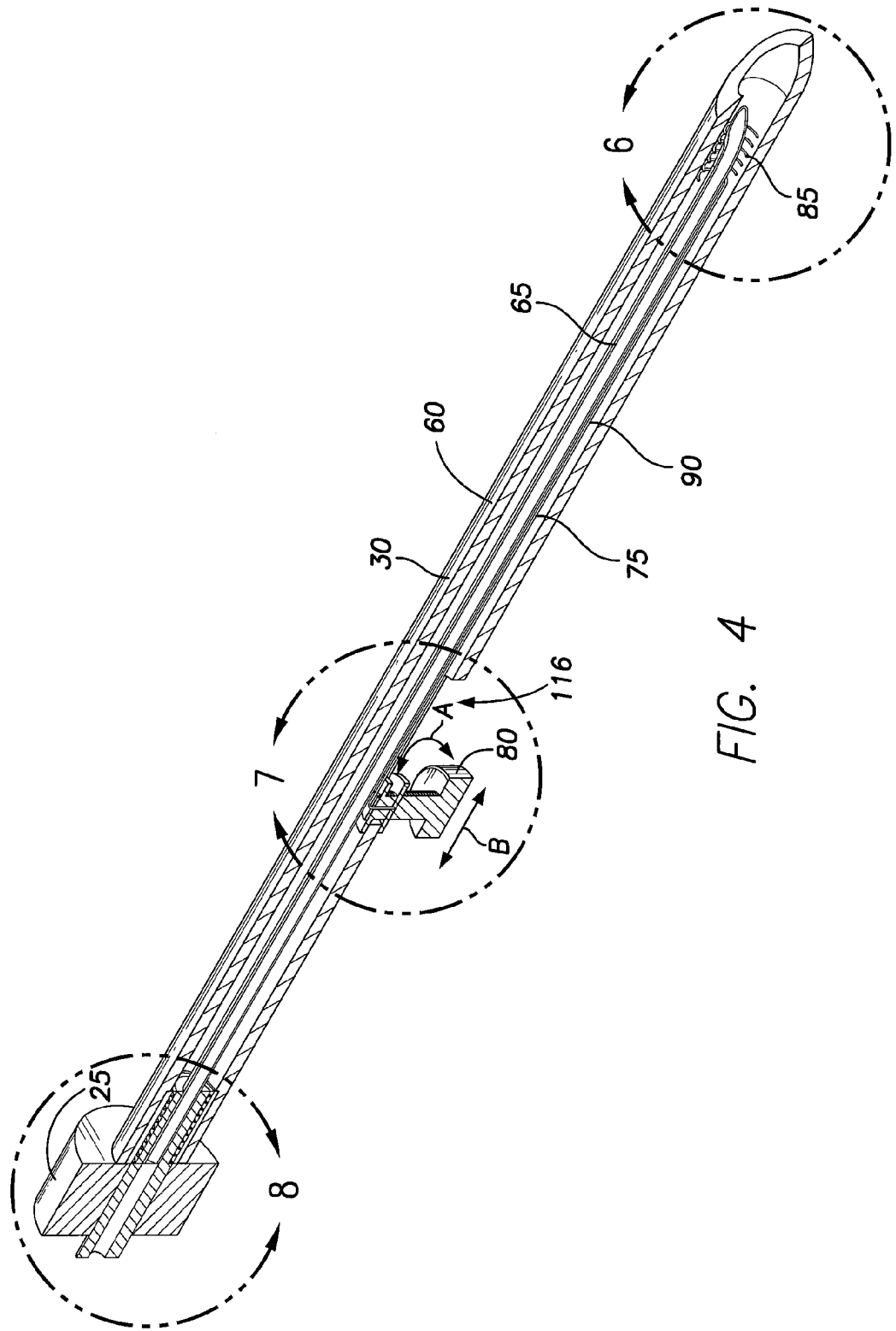
FIG. 4 is a longitudinal cross section of the view of the device depicted in FIG. 1.
Figure 5:
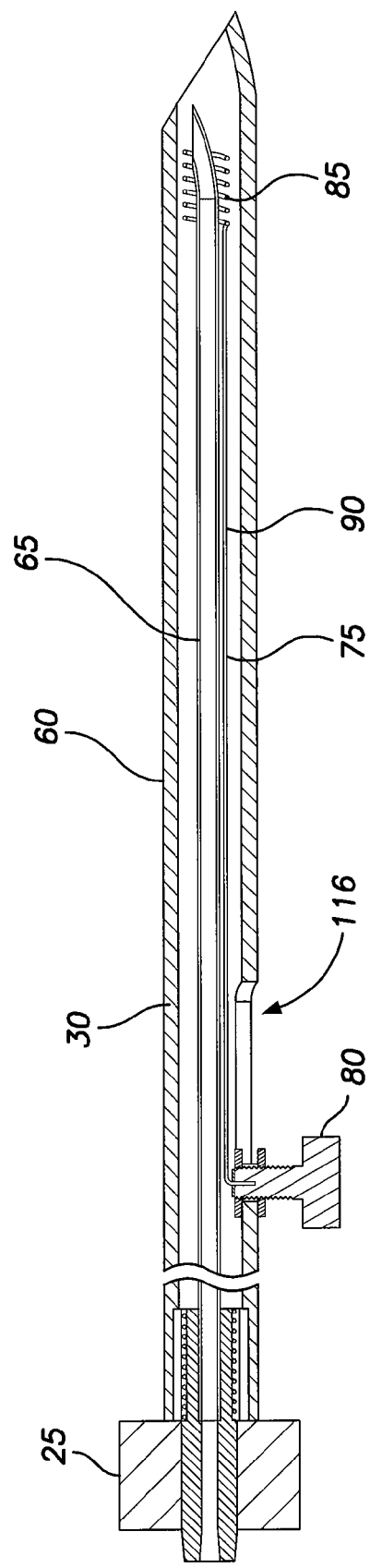
FIG. 5 is a longitudinal side elevation cross section of the device.

For a discussion of how each of the above-discussed elements are assembled together in the device 10, reference is made to FIGS. 4 and 5, which are, respectively, an isometric longitudinal cross section of the view of the device depicted in FIG. 1 and a longitudinal side elevation cross section of the device. As shown in FIGS. 4 and 5, the handle 25 is mounted on the proximal end of the tubular body assembly 30. The inner tubular body 65 is located within the outer tubular body 60 in a generally coaxial arrangement. The linear section 90 of the tissue engagement spring 75 extends generally parallel along the inner tubular body 65 from its connection to the knob 80 at the proximal end of the linear section 90 to the distal transition into the helical section 85 of the spring 75.

Figure 6:
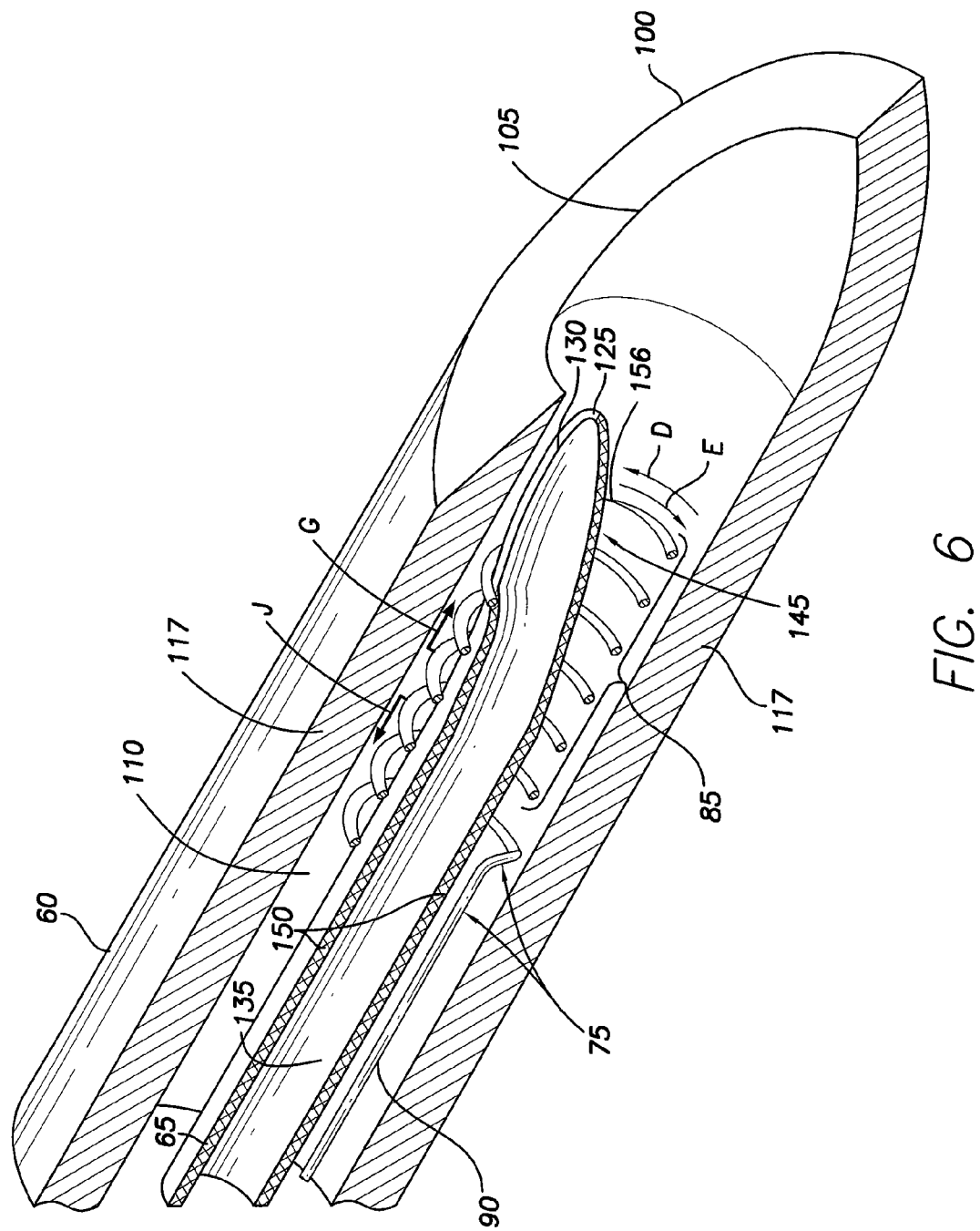
FIG. 6 is an enlarged view of the distal end of the device as depicted in FIG. 4.

As can be understood from FIGS. 4 and 5 and even more so from FIG. 6, which is an enlarged view of the distal end of the device 10 as depicted in FIG. 4, the helical section 85 of the spring 75 circumferentially extends about the distal end 125 of the inner tubular body 65 when the inner tubular body 65 and spring 75 are both in their respective retracted condition (i.e., most proximally positioned relative to the outer tubular body 60). When both the inner tubular body 65 and spring 75 are in their fully retracted conditions, the distal most portions of the inner tubular body and the spring are preferably fully recessed within the confines of the lumen 110 of the outer tubular body 60, thereby preventing the sharp distal point 156, e.g., the very distal end point, of the spring helical section 85 or the sharp distal tip 125 of the inner tubular body 65 from contacting tissue.

Figure 7:
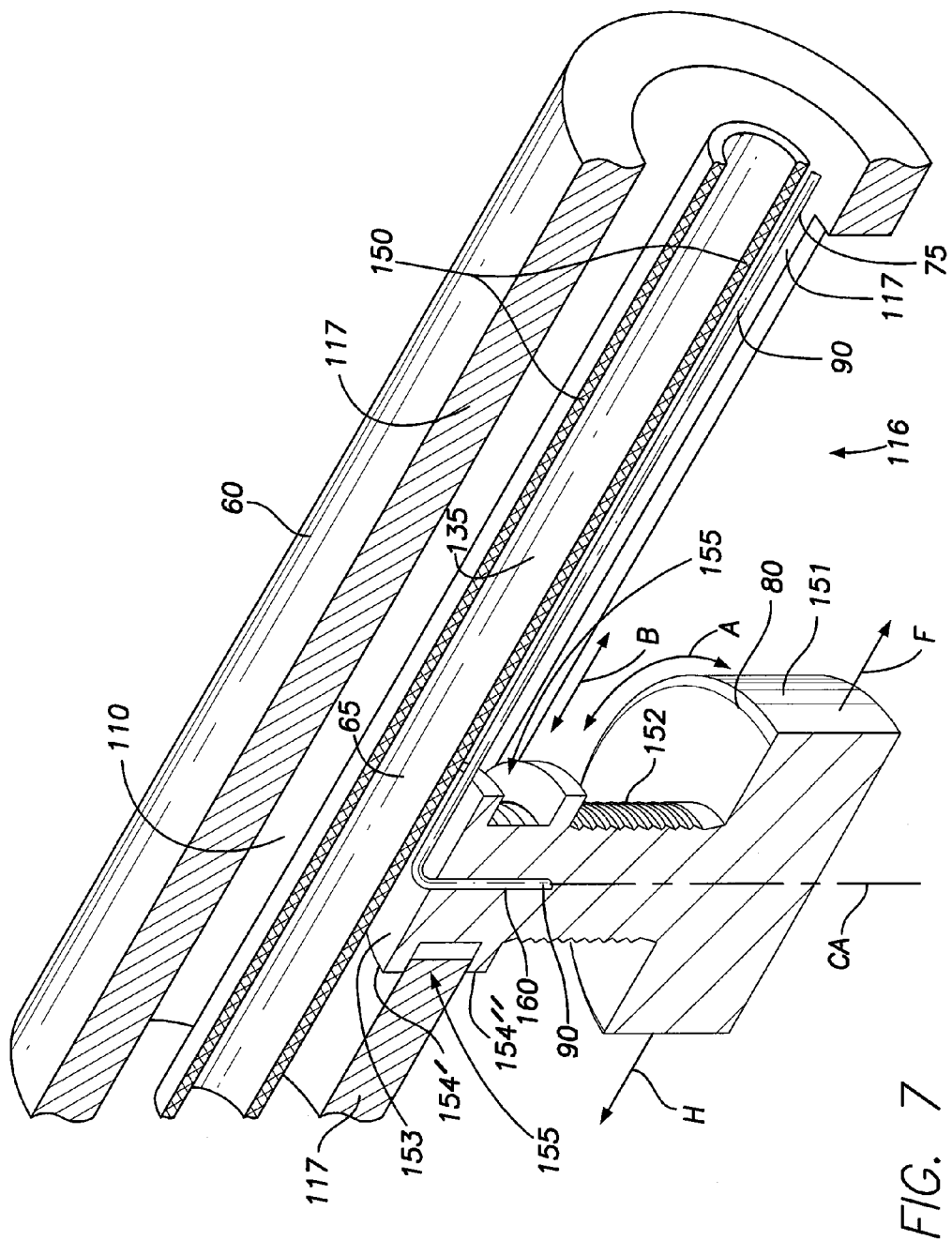
FIG. 7 is an enlarged view of the region occupied by the spring knob in FIG. 4.

As can be understood from FIGS. 4 and 5 and even more so from FIG. 7, which is an enlarged view of the region occupied by the spring knob 80 in FIG. 4, the knob 80 is received in the slot 116 in such a manner that the knob 80 is free to both rotate about the central longitudinal axis CA of the knob, as indicated by curved arrow A, and to slide along the slot 116 proximal-distal, as indicated by straight arrow B. The axis CA is generally perpendicular to the longitudinal central axis of the outer tubular body 60. The knob shaft 152 extends into the slot 116 of the outer tubular body 60. The gap 155, which is defined between the offset flanges 154', 154" radially extending from the shaft 152, receives the wall 117 of the outer tubular body 60 at the slot 116. Thus, the knob shaft 152 is coupled to the outer tubular body 60 in a manner that makes the knob shaft 152 rotatable within and linearly displaceable along the slot 116.

The proximal end 160 of the linear section 90 of the tissue engagement spring 75 extends into the knob shaft 152 generally coaxial with the central axis CA of the knob shaft 152. Thus, the spring linear section 90 extends generally parallel to and along the inner tubular body 65 until reaching the knob shaft free end 153, wherein the spring linear section 90 makes a generally right angle bend as the proximal end 160 of the spring linear section 90 extends along the shaft central axis CA into the knob shaft 152. The proximal end 160 may be held within the shaft 152 by being molded into the knob 80 or being connected via welding or an adhesive. Rotation of the knob 80 as indicated by arrow A will result in rotation of the spring linear section 90 about the longitudinal axis of the spring linear section 90. Such rotation of the spring linear section 90 will cause the spring helical section 85 to rotate about the longitudinal axis of the spring helical section 85.

As can be understood from FIG. 6, if the rotation of the spring helical section 85 is in a first direction, as indicated by arrow D, the sharp distal tip 156 of the helical section 85 will penetrate tissue and allow the helical section to screw into the tissue as discussed below. If the rotation of the spring helical section 85 is in a second direction opposite from the first direction, as indicated by arrow E, the sharp distal tip 156 of the helical section 85 will withdraw from tissue and allow the helical section to unscrew from the tissue as discussed below.

If the knob 80 is displaced distally along the slot 116 as indicated by arrow F in FIG. 7, then the spring helical section 85 will be caused to extend distally along the length of the outer tubular body from the distal opening 105 of the outer tubular body 60 as indicated by arrow G in FIG. 6. If the knob 80 is displaced proximally along the slot 116 as indicated by arrow H in FIG. 7, then the spring helical section 85 will be caused to retract proximally along the length of the outer tubular body back into the lumen 110 of the outer tubular body 60 as indicated by arrow J in FIG. 6.

Figure 8:
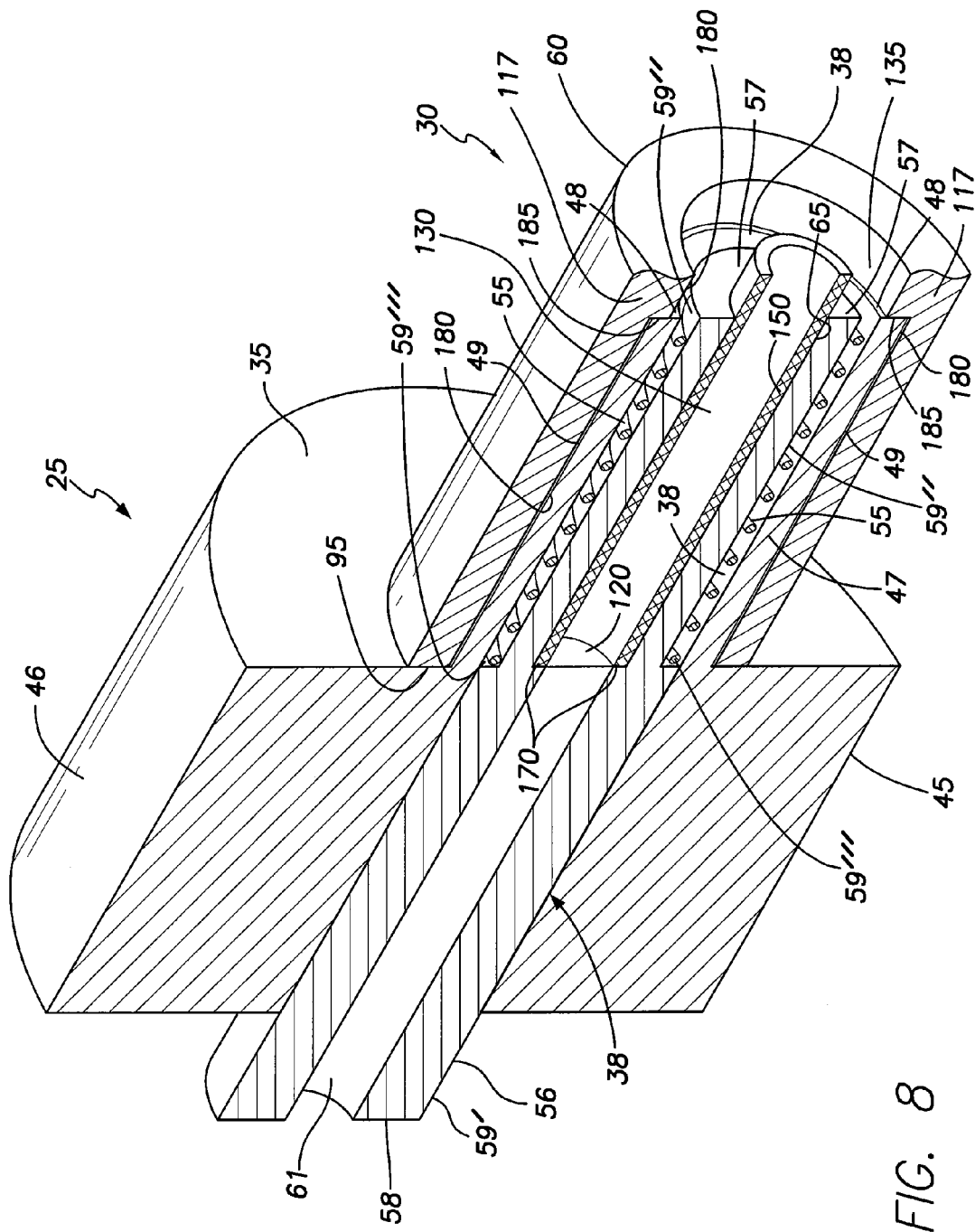
FIG. 8 is an enlarged view of the region occupied by the handle 25 in FIG. 4.

As can be understood from FIGS. 4 and 5 and even more so from FIG. 8, which is an enlarged view of the region occupied by the handle 25 in FIG. 4, the element of the handle 25 connected to the elements of the tubular body assembly 30 in a coaxial arrangement. Specifically, the proximal end 120 of the inner tubular body 65 is received in a distal half of the lumen 61 of the button 56, the proximal end 120 abutting against an internal shoulder 170 in the lumen button lumen 61 such that the lumen 130 of the inner tubular body 65 forms a generally iso-diametric lumen with the half of the button lumen 61 proximal the shoulder 170. The proximal region of the inner tubular body received in the distal half of the button lumen 61 may be secured to the button lumen 61 via threads, welding, adhesive, being molded into the button lumen, etc. The inner tubular body and button are coaxial about the longitudinal center axis of the inner tubular body.

As indicated in FIGS. 4, 5 and 8, the helical spring 55 extends in a coaxial manner about the outer circumferential surface of the small diameter region 59" of the button, a proximal end of the spring 55 abutting against the shoulder 59''' of the button 56 and a distal end of the spring 55 abutting or acting against a portion of a proximal region of the outer tubular body 60 or a portion of a distal face 48 of the outer handle portion 45. As a result, the spring 55 is positioned to act between the outer handle portion 45 and the button 56 such that the spring 55 biases the button 56 to proximally extend from the outer handle portion 45 when not acted upon, as best illustrated in FIGS. 2, 4, 5 and 8.

As indicated in FIGS. 4, 5 and 8, the button 56, with the spring 55 and inner tubular body 65 connected to the button as described above, is coaxially received in the shaft 38 of the outer handle portion 45 such that the spring 55 and the button small diameter region 59" supporting the spring 55 are located in the part of the shaft 38 within the small diameter cylindrical portion 47 of the outer handle portion 45. The large diameter region 59' of the button 56 resides in the part of the shaft 38 within the large diameter cylindrical portion 46 of the outer handle portion 45, the most proximal portion of the button proximally projecting out of the outer handle portion. The button 56 is slidable within the shaft 38 such that the button 56, and the inner tubular body 65 connected to and distally extending from the button 56, can be acted upon at the button distal end 58 to be caused to compress the spring 55 and displace distally within the outer handle portion 45. Such distal displacement of the button against the spring 55 causes the inner tubular body 65 to displace distally within the outer tubular body 60 such that the inner tubular body distal end 125 distally projects from the distal opening 105 of the outer tubular body 60.

As indicated in FIGS. 4, 5 and 8, the small diameter cylindrical portion 47 is received in the proximal end of the interior of the outer tubular body 60 such that the outer circumferential surface 49 of the small diameter cylindrical portion 47 is in generally coextensive contact with the inner circumferential surface 180 of the outer tubular body 60. A distal face 48 of the outer handle portion 45 abuts against a shoulder 185 defined in the inner circumferential surface 180 of the outer tubular body 60, and the proximal end of the outer tubular body 60 abuts against the distal face 35 of the outer tubular body 60.

The small diameter cylindrical portion 47 of the outer handle portion 45 is received in the proximal end of the interior of the outer tubular body 60 and secured in such an arrangement via threads, welding, adhesive, being molded into the interior of the outer tubular body 60, etc. The outer tubular body 60 and outer handle portion 45 are coaxial about the longitudinal center axis of the outer tubular body. The button 56 and outer handle portion 45 and the inner tubular body 65 and the outer tubular body 60 are all coaxial to each other about a common longitudinally extending center axis of the device 10.

Figure 9:
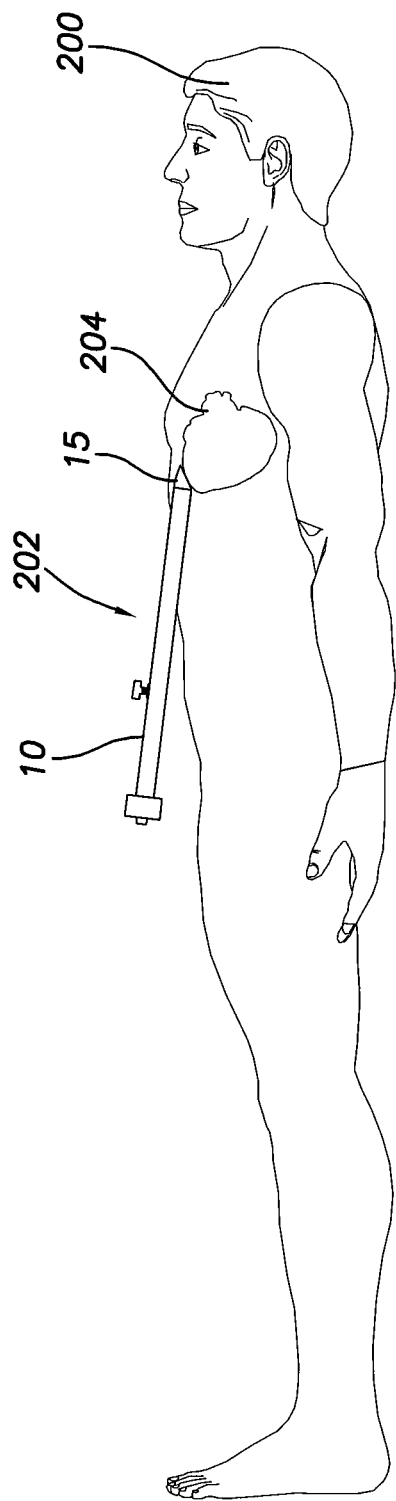
FIG. 9 is a side elevation of a patient with the device inserted in the patient such that the distal end of the device is adjacent the surface of the patient heart.

For a discussion of a method of employing the device 10 to establish a pathway for delivering a medical treatment or device to the intrapericardial space of a patient, reference is made to FIG. 9, which is a side elevation of a patient 200. As shown in FIG. 9, the distal end 15 of the device 10 is inserted into the patient via a sub-xiphoid access 202 to place the distal end 15 adjacent the patient's heart 204. The pointed distal end 100 (FIG. 1) of the outer tubular body 60 may be employed to create the sub-xiphoid access 202, or the access 202 may be created with a scalpel or other instrument, the device 10 then being inserted through the opening created by the scalpel.

Figure 10:
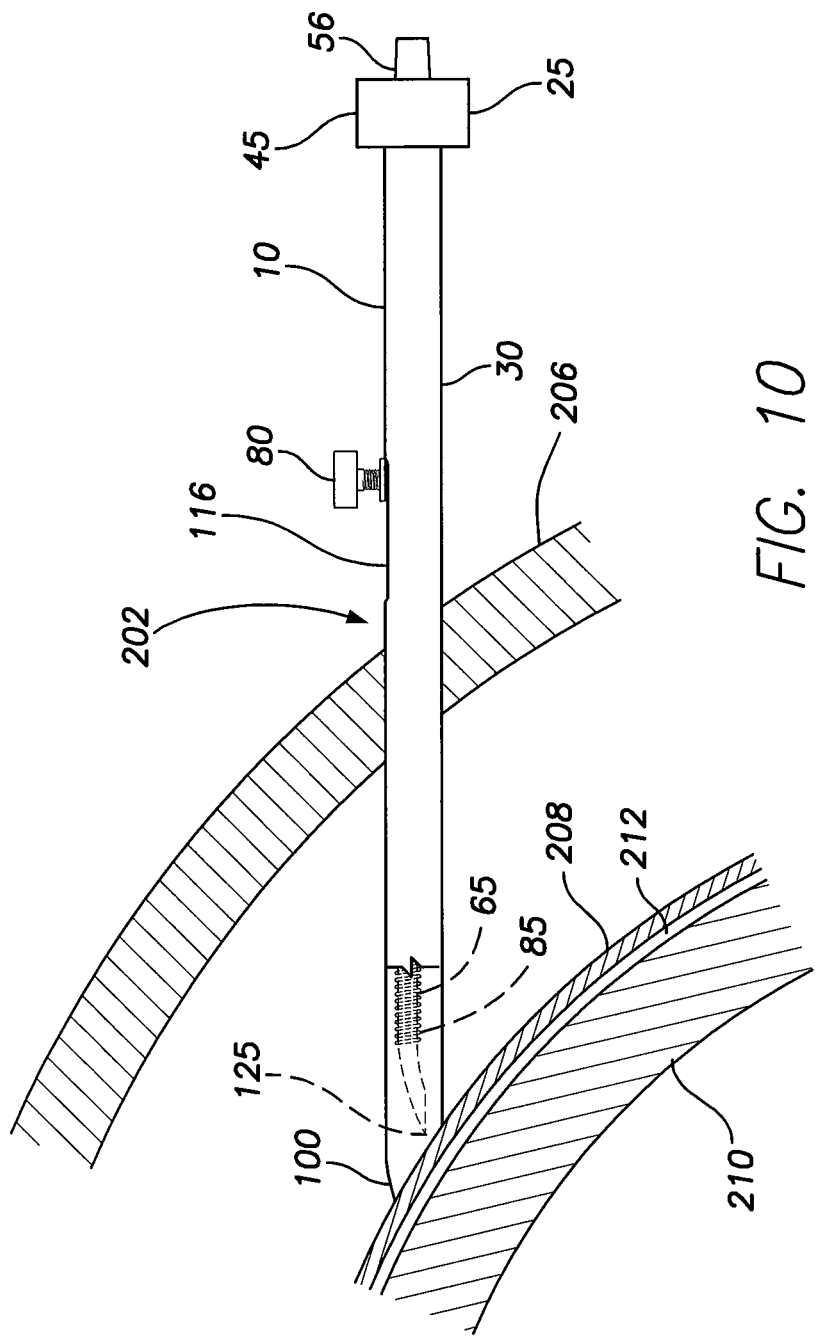
FIGS. 10-16 are enlarged views of the device adjacent the patient heart as depicted in FIG. 9, each of FIGS. 10-16 illustrating a step in a series of successive steps where the device is used to deliver a stylet, guidewire, etc. to the intrapericardial space.

As can be understood from FIG. 10, which is the same view as FIG. 9, except enlarged to focus on the operation of the device 10, the tubular body assembly 30 extends through the patient check wall 206 via the sub-xiphoid access 202. The beveled end 100 of the outer tubular body 60 is placed against the exterior surface of the pericardial sac 208, which, along with the adjacent heart wall 210, defines the intrapericardial space 212. As shown in FIG. 10, the button 56 has not been acted upon and is biased as proximal as possible by the helical spring 55 in the handle 25 and, as a result, the sharp distal tip 125 of the inner tubular body 65 is located completely within the lumen 110 of the outer tubular body 60. Also, the spring knob 80 is located as proximal as possible within the slot 116 such that the helical tissue spring 85 is located completely within the lumen 110 of the outer tubular body 60.

Figure 11:
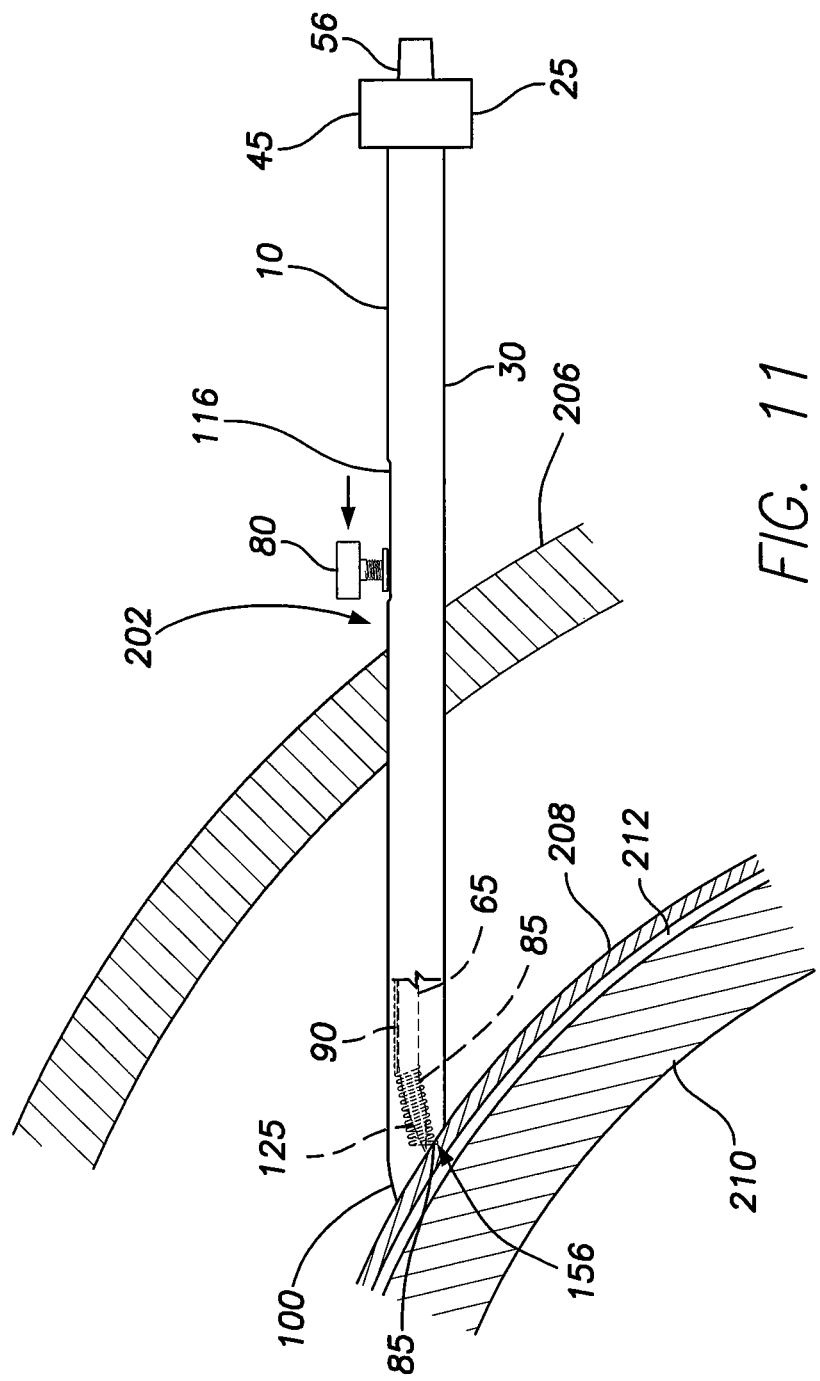

As indicated in FIG. 11, the spring knob 80 is fully distally displaced within the slot 116, thereby causing the distal tip 156 of the helical tissue spring 85 to distally displace (independent of any rotation of the helical tissue spring 85) along the length of the outer tubular body 60 and distally protrude from the distal opening 105 in the outer tubular body 60. The distal tip 156 of the helical tissue spring 85 is now in contact the surface of the pericardial sac 208.

Figure 12:
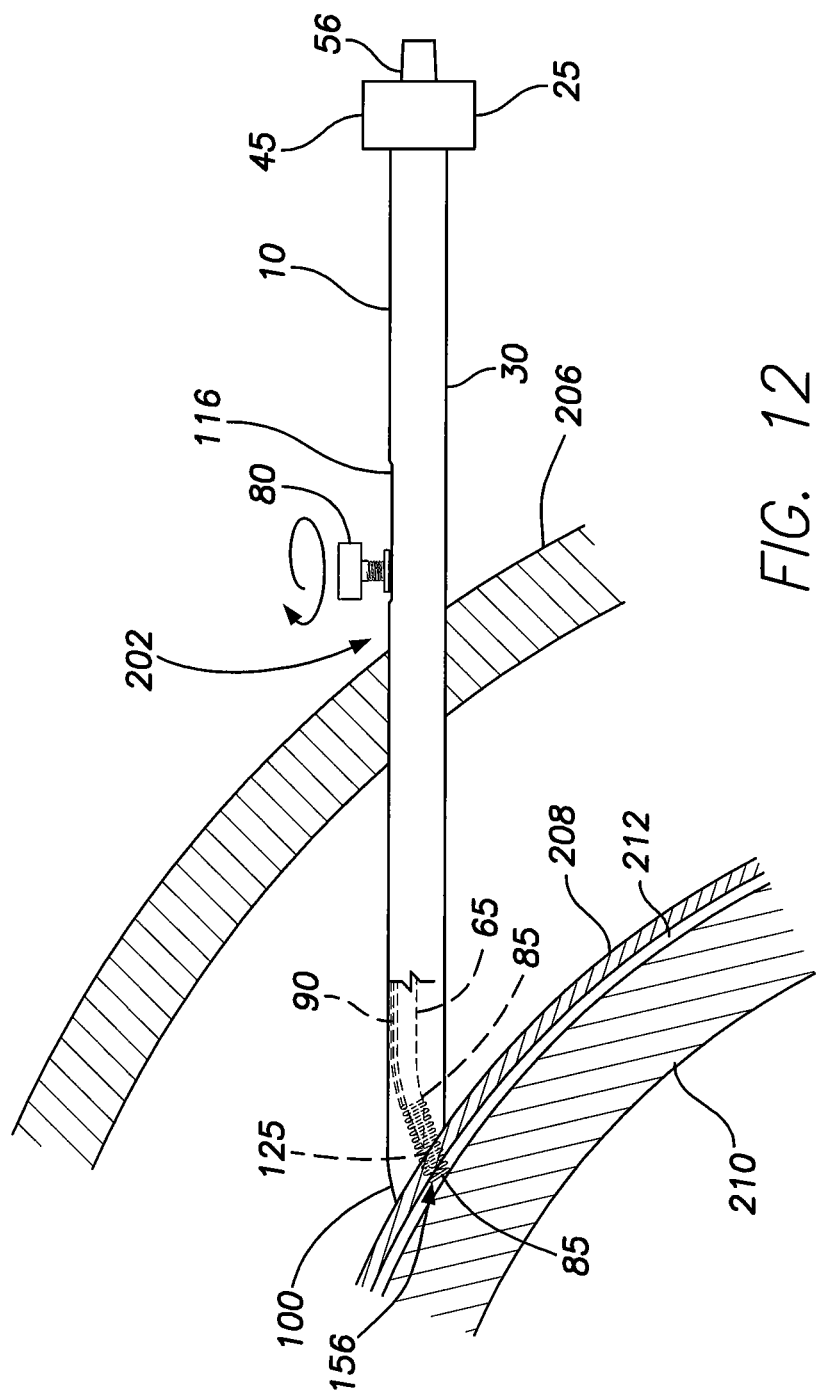

As depicted in FIG. 12, the spring knob 80 is rotated while in its most distal position established in FIG. 11. The rotation of the spring knob 80 causes the helical tissue spring 85 to rotate about its axis and the distal tip 156 of the helical tissue spring 85 to screw into the pericardial sac. In one embodiment, the helical tissue spring 85 is configured to screw into the pericardium a maximum depth of approximately 6 mm to approximately 8 mm, or less.

Figure 13:
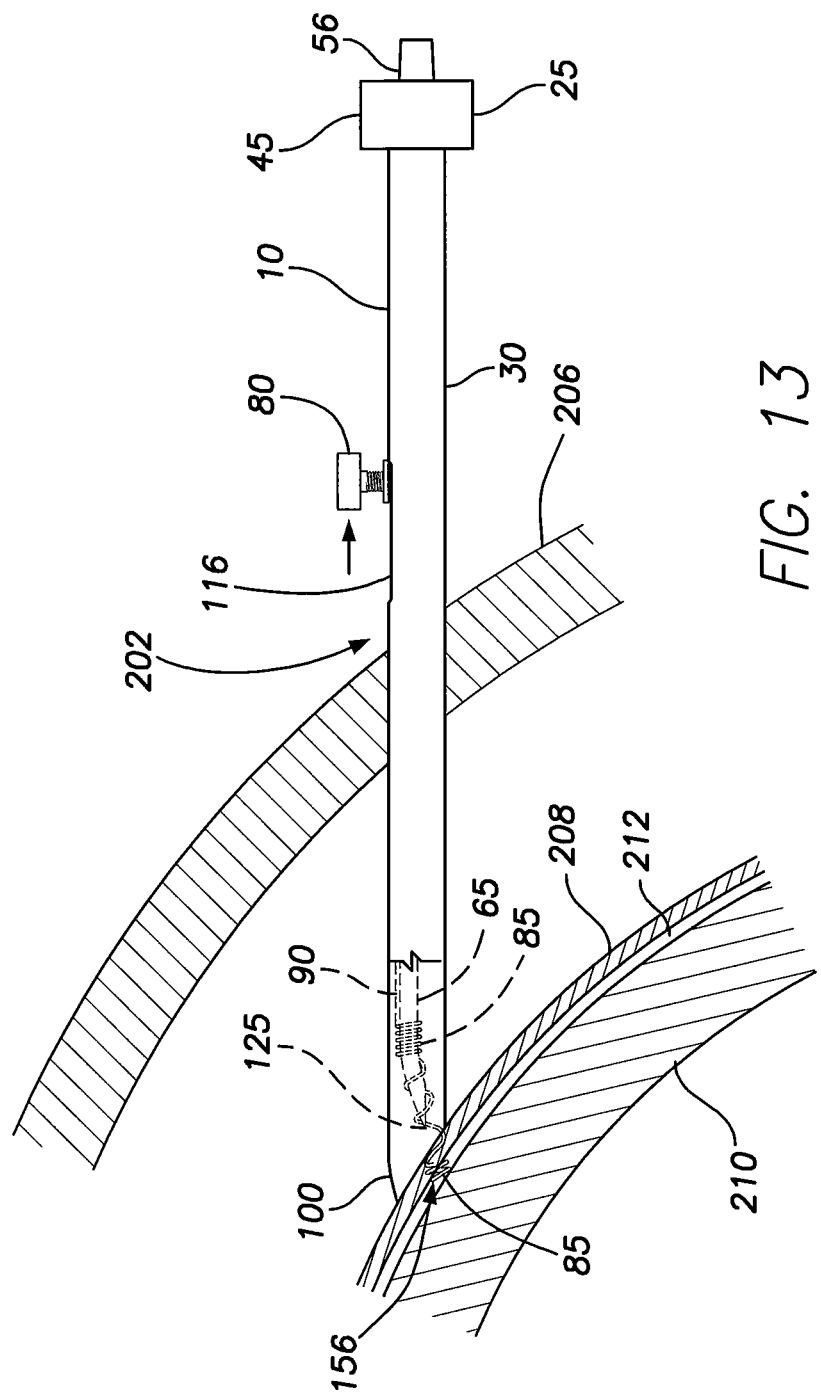
Figure 14:
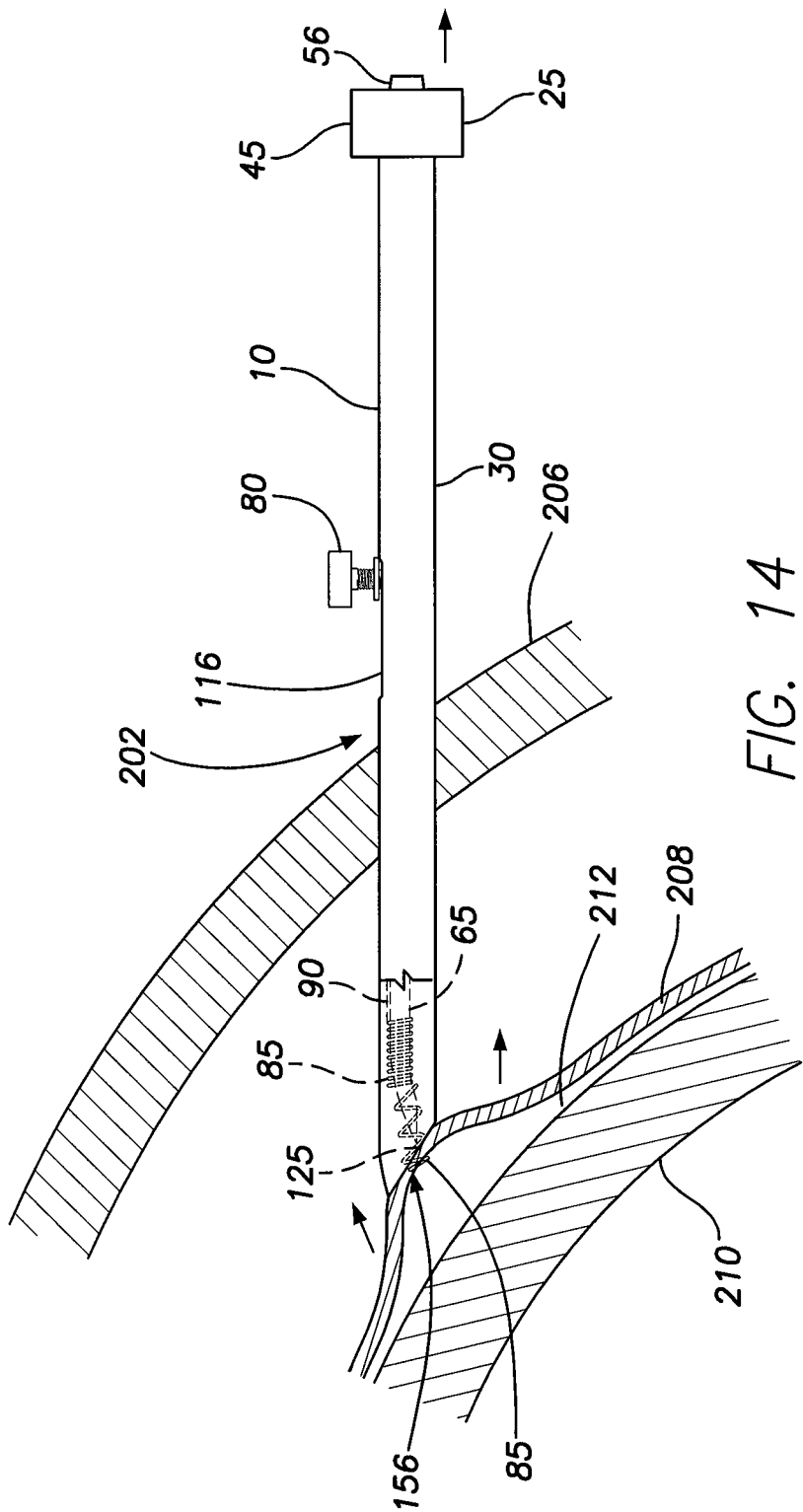

As illustrated in FIG. 13, the spring knob 80 is fully proximally displaced within the slot 116, causing the helical tissue spring 85 to proximally displace (independent of any rotation of the helical tissue spring 85) along the length of the outer tubular body and retract at least partially back into the lumen 110 of the outer tubular body 60. The pericardial sac 208 is now pinched between the distal end 100 of the outer tubular body 60 and the helical coils of the spring 85 screwed into the pericardial sac 208. The entire device 10 is then proximally displaced relative to the heart wall 210, thereby pulling the pericardial sac 208 away from the surface of the heart wall 210, as indicated in FIG. 14.

Figure 15:
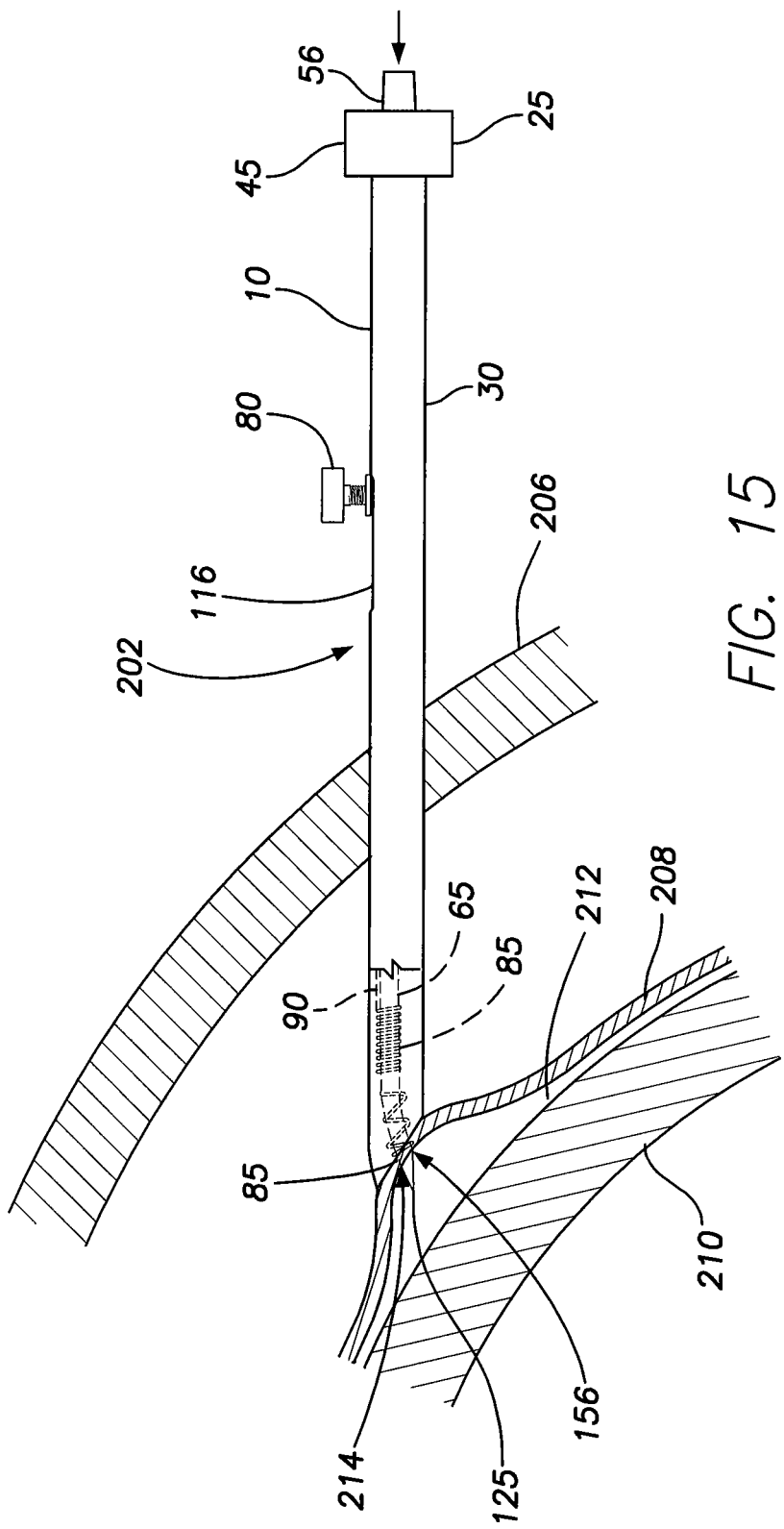

As shown in FIG. 15, the button 56 is distally displaced into the outer handle portion 45 of the handle 25, causing the sharp distal tip 125 of the inner tubular body 65 to distally project out of the distal opening 105 of the outer tubular body 65. As a result, the sharp distal tip 125 of the inner tubular body 65 extends through the coils of the helical tissue spring 85 screwed into the pericardial sac 208, the sharp distal tip 125 of the inner tubular body 65 penetrating the pericardial sac 208 and establishing an opening 214 into the intrapericardial space 212.

Figure 16:
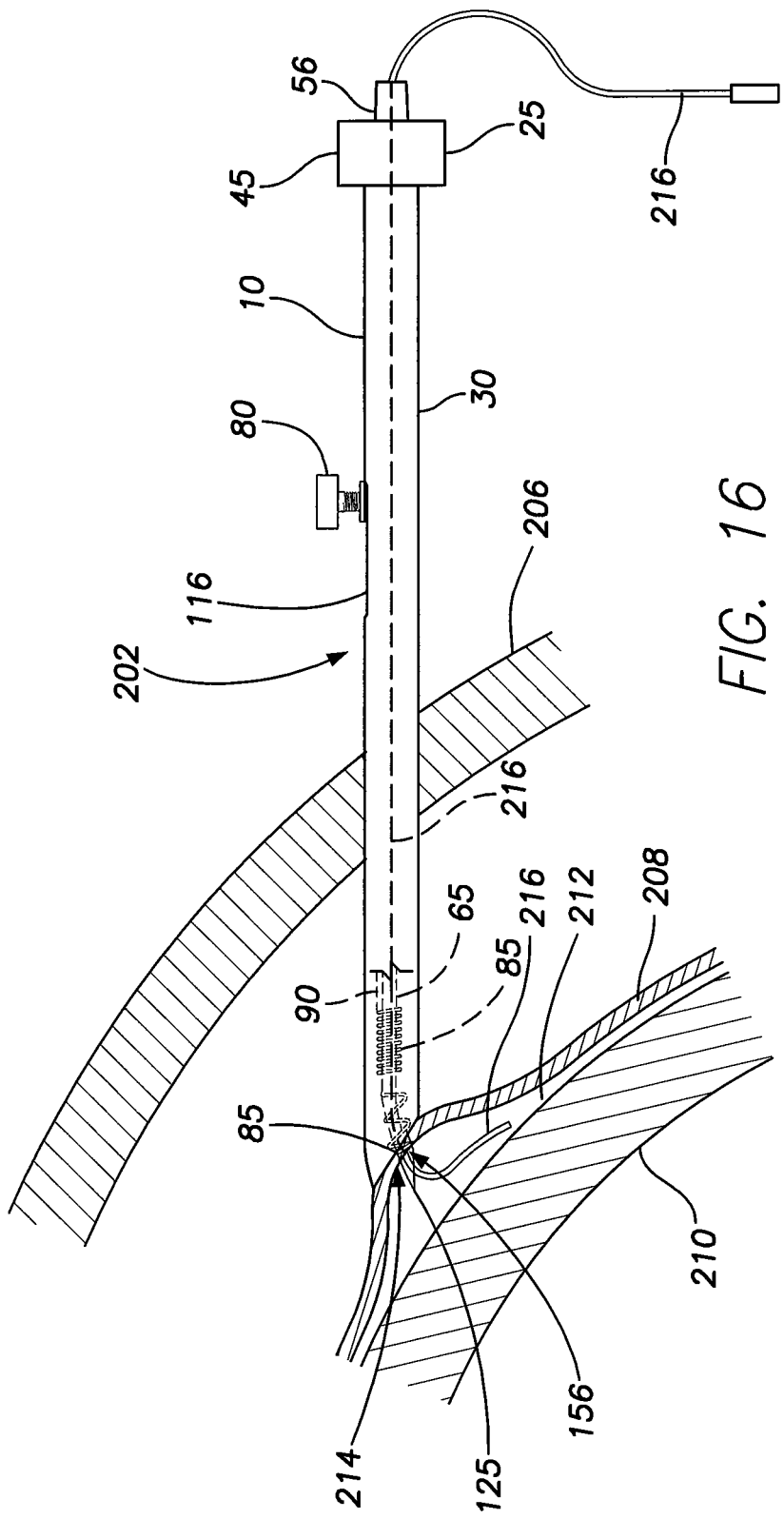

As indicated in FIG. 16, a guidewire, stylet, catheter, medicament delivery device, etc. 216 may be fed through the lumens 61, 135 of the button 56 and inner tubular body 65 and into the intrapericardial space 212. The device 10 may be removed from the patient by reversing the order of the process depicted in FIGS. 10-16.

In one embodiment, if it is a guidewire or stylet 216 that has been delivered to the intrapericardial space via the device 10 as described above with respect to FIGS. 10-16, then the device may be removed from about the guidewire or stylet 216, leaving the stylet or guidewire 216 extending from the sub-xiphoid access 202 into the intrapericardial space 212 to act as a pathway to the intrapericardial space 212 from the exterior of the patient 200. Introducer sheaths, catheters or other devices may then be tracked over the stylet or guidewire 216 into the intrapericardial space 212.

Figure 17:
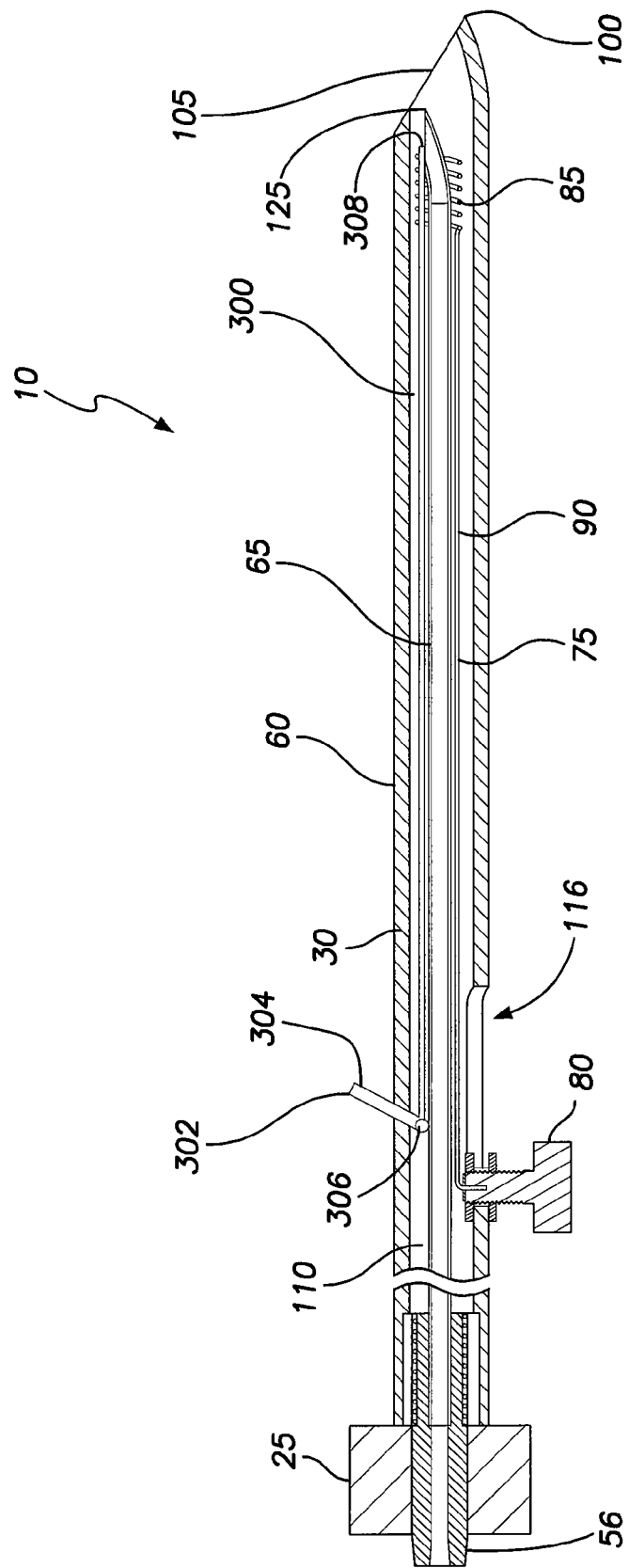
FIGS. 17-18 are the same as FIG. 5, except of another embodiment of the device employing a separate pinching member for acting with the helical tissue engagement spring to pinch a pericardial sac.

As shown in FIG. 17, which is the same view as FIG. 5, except of the second embodiment of the device 10, the device is generally the same as described above, except the device 10 has a spring loaded inner tubular body 65 and a pinching member 300 separately operated from the spring knob 85. Specifically, the device 10 is a needle spring holder including the helical tissue spring 85 as described above with respect to FIGS. 1-8, a latching or pinching member 300, the spring control knob 80 as described above with respect to FIGS. 1-8, and the inner tubular body 65 as described above, except configured for a spring-loaded release. The pinching member 300 is part of a pinching member assembly 302 that includes the pinching member 300 and an actuation lever 304 pivotally coupled to the outer tubular body at a proximal end 306 of the pinching member 300. The pinching member 300 is located in the lumen 110 of the outer tubular body 60 and is a longitudinally extending member that runs generally parallel to the inner tubular body 65 to distally terminate in a blunt distal end 308.

When in a non-engaged state, the pinching member 300 is recessed within the opening 105 of the distal end 100 of the outer tubular body 60. As can be understood from FIG. 18, which is the same view as FIG. 17, when the pinching member lever 304 is tilted proximally, the pinching member 300 is caused to distally displace within the outer tubular body 60. Thus, when the helical tissue spring 85 has been screwed into the pericardium 208 such that the pericardium is in close proximity to, if not abutting, the distal end 100 of the outer tubular body 60, the distal end 308 of the pinching member 300 can be caused to at least partially extend beyond the distal end of the outer tubular body 60 so as to pinch the pericardium 208 against the screwed-in helical spring 85.

Once the pericardium 208 is pinched between the screwed-in helical spring 85 and the pinching member distal end 308, the pericardium can be pulled away from the underlying surface of the heart wall 210 as described above. The button 56 can then be pushed to release an engagement feature 310 (e.g., latch, engagement tooth, etc.) that maintains the inner tubular body 65 recessed within the outer tubular body 60, against the outward bias of the helical spring 55. Upon release of the engagement feature 310, the spring launches the inner tubular body 65 distally, such that the distal tip 125 of the inner tubular body 65 is caused to protrude quickly from the distal opening 105 of the outer tubular body. The distal tip 125 extends through the coils of the helical spring 85 to penetrate the pericardial sac 208, as described above. A guidewire, stylet, etc. can then be routed through the inner tubular body and into the pericardial space 212 as described above.

Figure 18:
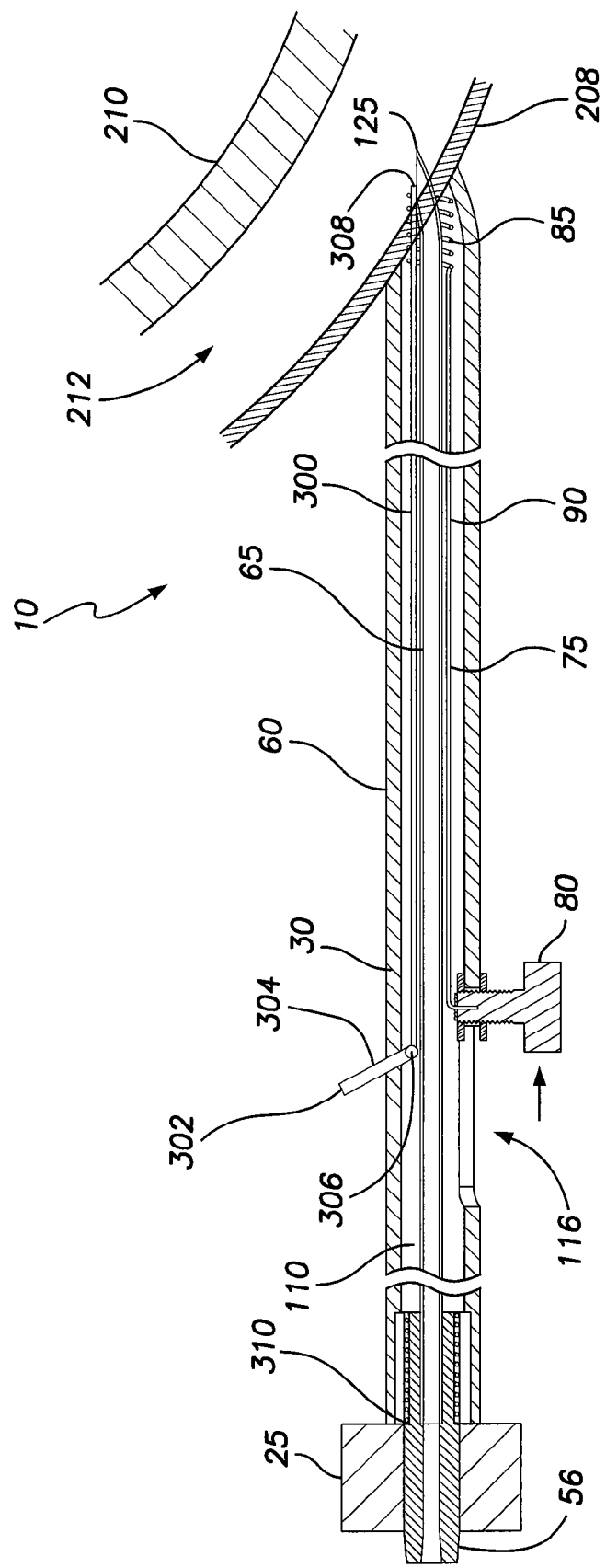

The stroke of the inner tubular body 65, whether in the context of the embodiment discussed with respect to FIGS. 1-8 or the embodiment discussed with respect to FIGS. 17-18, is approximately 8 mm or less. In other words, the distal tip 125 of the inner tubular body will only extend from the distal opening 105 of the outer tubular body 60 approximately 8 mm or less.

Figure 19:
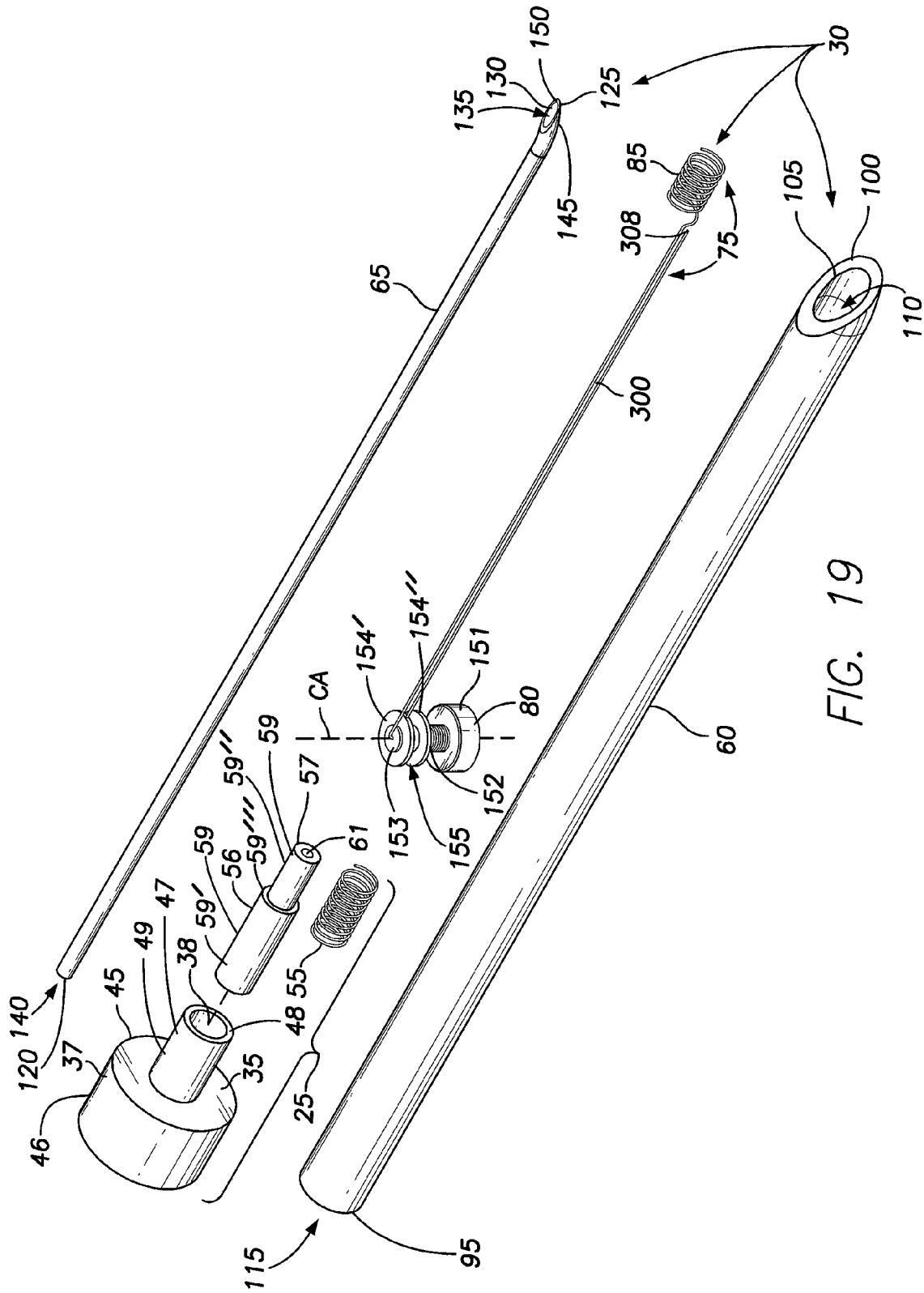
FIGS. 19, 20 and 21 are respectively the same as FIGS. 3, 6 and 7, except of an embodiment of the device employing a pinching member that is part of the engagement spring assembly and which acts with the helical tissue engagement spring to pinch a pericardial sac.
Figure 20:
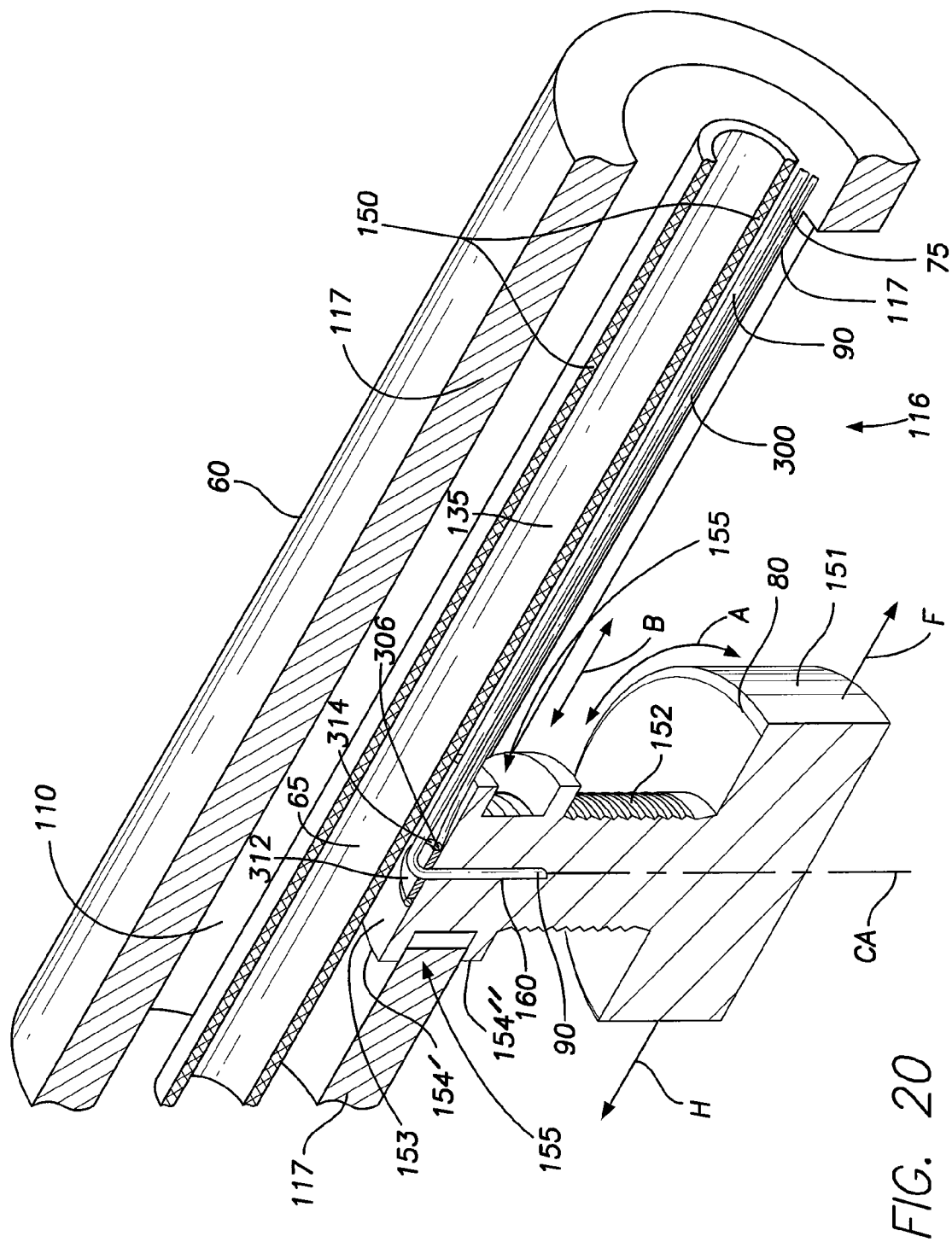
Figure 21:
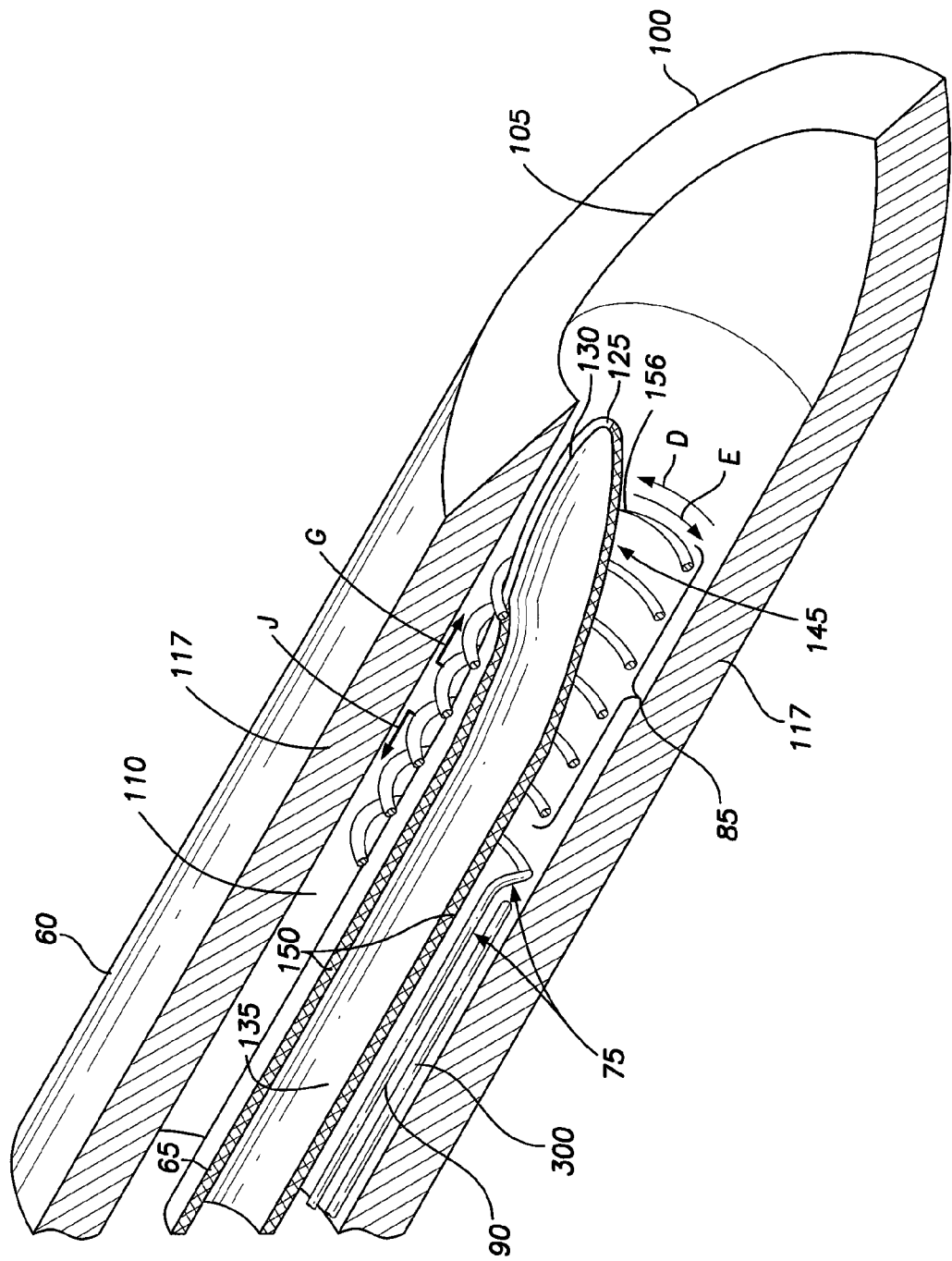

As can be understood from FIGS. 19, 20 and 21, which are respectively the same as FIGS. 3, 6 and 7, except of the third embodiment of the device 10, the pinching member 300 is part of the engagement spring assembly 70 and acts with the helical tissue engagement spring 85 to pinch a pericardial sac 208. Specifically, as shown in FIG. 19, the pinching member 300, also referred to as a longitudinally extending member, has a proximal end 306 coupled to the knob 80 and a blunt distal end 308 near the distal end of the outer tubular body 60. The member 300 extends generally parallel to the straight portion 90 of the spring 75 extending between the knob 80 and the helical portion 85.

As shown in FIG. 20, the configuration and aspects of the spring assembly 70 are generally the same as described above with respect to FIG. 1-8, except the proximal end 306 of the member 300 is pivotally coupled about a bearing surface 312 on the free end 153 of the knob 80. As a result, the knob can be rotated as depicted by arrow A to cause the straight portion 90 of the spring 75 to rotate, thereby causing the helical portion 85 to rotate, as can be understood from FIG. 21. However, the bearing surface 312 simply rotates within a circular bearing portion 314 of the member proximal end 306 such that the member 300 is not displaced by rotation of the knob 80.

The third embodiment is employed in much the same manner as described above with respect to FIGS. 9-16, except as now described. First, the helical portion 85 is caused to screw into the pericardial sac 208 by distally displacing the knob 80 only a portion of the full distance of the slot 116, the portion of the distance being just sufficient to cause the sharp tip 156 of the helical portion 85 to contact the pericardial sac 208. The knob is then fully rotated to cause the helical portion 85 to fully screw into the pericardial sac.

Once the helical portion 85 is screwed into the pericardial sac, then the knob 80 can be more completely distally displaced within the slot 116 such that the blunt distal end 308 of the pinching member 300 finally abuts against the tissue engaged by the screwed-in helical portion 85. The pericardial sac is now pinched between the screwed-in helical portion 85 and the blunt end 308 of the pinching member 300. The device 10 can then be used to pull the pericardial sac 208 away from the surface of the heart wall.

With the pericardial sac safely spaced away from the heart wall surface, the inner tubular body 65 can then be distally displaced, either as discussed with respect to FIGS. 1-8 wherein the button is pushed to distally drive the inner tubular body 65 or as discussed with respect to FIGS. 17-18 wherein the button simply releases a catch 310 that allows the inner tubular body 65 to be biased forward via spring loading. In either case the distal tip 125 of the inner tubular body 65 penetrates the pericardial sac, as discussed above with respect to FIGS. 9-16.

While the preceding discussion is given in the context of the device 10 being configured for, and used in the context of, accessing an intrapericadial space, the device 10 or other embodiments of the device may readily be employed for other surgical procedures. For example, the tubular body assembly 30 could be flexible and substantially longer than they are wide for be trackable into the right atrium or right ventricle via the subclavian vein. Such a device 10 could then be employed to engage and work on the septum between the right and left atriums or right and left ventricles. The helical tissue screw 85 and distal tip 125 of the inner tubular member 65 could be configured for tissue penetration of approximately 6 mm or approximately 8 mm or less.

In one embodiment, the device 10 is configured for epidural use in delivering a spinal block in a neural space. In such an embodiment, the helical tissue screw 85 and distal tip 125 of the inner tubular member 65 could be configured for tissue penetration of approximately 1 mm or approximately 2 mm or less.

Although the present invention has been described with reference to preferred embodiments, persons skilled in the art will recognize that changes may be made in form and detail without departing from the spirit and scope of the invention.

What is claimed is:

1. A medical device configured to engage and penetrate a pericardial sac, said device comprising:
    an outer tubular body comprising a proximal end, a distal end and a first lumen extending between the ends;
    an inner tubular body comprising a proximal end and a distal end and a second lumen extending between the ends, the inner tubular body located in the lumen of the outer tubular body, the proximal end of the inner tubular body operably coupled to the proximal end of the outer tubular body, the distal end of the inner tubular body being extendable out of the distal end of the outer tubular body and defining an opening sized for passage of a guidewire through the second lumen and the opening; and
    a helical tissue engagement member having a longitudinal axis, the engagement member:
        displaceable along the length of the outer tubular body from a first position to a second position, the first position being in the lumen of the outer tubular body recessed relative to the distal end of the outer tubular body, and the second position extending out of the distal end of the outer tubular body and displaceable relative to the inner tubular body; and
        rotatable about the longitudinal axis and relative to the outer tubular body wherein the inner tubular body in the vicinity of the distal end of the inner tubular body extends through at least one coil of the helical tissue engagement member.

2. The device of claim 1, wherein the inner tubular body in the vicinity of the distal end of the inner tubular body extends through the at least one coil of the helical tissue engagement member when the inner tubular body is extended out of the distal end of the outer tubular body and the helical tissue engagement member is in its second position.

3. The device of claim 1, wherein the inner tubular body in the vicinity of the distal end of the inner tubular body extends through the at least one coil of the helical tissue engagement member when the inner tubular body is not extended out of the distal end of the outer tubular body and the helical tissue engagement member is in its first position.

4. The device of claim 1, wherein the distal end of the outer tubular body comprises a beveled end.

5. The device of claim 4, wherein the beveled end is between approximately 35 degrees and approximately 45 degrees of being parallel with a longitudinal center axis of the outer tubular body.

6. The device of claim 1, wherein the distal end of the inner tubular body includes a distal opening that opens in a direction that is generally perpendicular to a longitudinal center axis of the inner tubular body.

7. The device of claim 1, wherein the inner tubular body is spring biased to displace distally relative to the outer tubular body.

8. The device of claim 1, further comprising a pinching member in the lumen of the outer tubular body and comprising a distal end, wherein the pinching member is configured to pinch the pericardial sac between the distal end of the pinching member and a portion of the helical tissue engagement member.

9. The device of claim 1, wherein the helical tissue engagement member is at least partially positioned between the inner tubular body and the outer tubular body.

10. The device of claim 1, further comprising a handle operably coupling the proximal end of the inner tubular body to the proximal end of the outer tubular body.

* * * * *